(12) United States Patent
Fischell et al.

(10) Patent No.: US 9,585,781 B2
(45) Date of Patent: Mar. 7, 2017

(54) STENT DELIVERY CATHETER WITH BALLOON CONTROL BANDS

(71) Applicant: Svelte Medical Systems, Inc., New Providence, NJ (US)

(72) Inventors: Robert E. Fischell, Dayton, MD (US); David R. Fischell, Fair Haven, NJ (US); Fernando DiCaprio, St. Paul, MN (US)

(73) Assignee: Svelte Medical Systems, Inc., New Providence, NJ (US)

( * ) Notice: Subject to any disclaimer, the term of this patent is extended or adjusted under 35 U.S.C. 154(b) by 0 days.

(21) Appl. No.: 15/085,281

(22) Filed: Mar. 30, 2016

(65) Prior Publication Data
US 2016/0206454 A1 Jul. 21, 2016

Related U.S. Application Data

(60) Continuation of application No. 14/714,639, filed on May 18, 2015, now Pat. No. 9,387,103, which is a (Continued)

(51) Int. Cl.
*A61F 2/958* (2013.01)
*A61M 25/10* (2013.01)
*A61M 25/01* (2006.01)

(52) U.S. Cl.
CPC ........... *A61F 2/958* (2013.01); *A61M 25/104* (2013.01); *A61M 25/1027* (2013.01);
(Continued)

(58) Field of Classification Search
CPC ........... A61F 2/958; A61F 2002/9583; A61M 25/1027; A61M 25/1034; A61M 25/104;
(Continued)

(56) References Cited

U.S. PATENT DOCUMENTS

| 5,318,529 A | 6/1994 | Kontos |
| 5,409,495 A | 4/1995 | Osborn |

(Continued)

FOREIGN PATENT DOCUMENTS

EP 1208815 A2 5/2002

OTHER PUBLICATIONS

International Search Report for Application PCT/US2010/028581 dated Jun. 2, 2010.
(Continued)

*Primary Examiner* — Katrina Stransky
(74) *Attorney, Agent, or Firm* — Honigman Miller Schwartz and Cohn LLP

(57) ABSTRACT

A stent delivery catheter including a catheter tubing defining a lumen therethrough, a balloon disposed near a distal end of the catheter tubing and moving between deflated and inflated states, and proximal and distal balloon control bands concentrically arranged around respective proximal and distal end portions of the balloon. The proximal balloon control band has a proximal end located proximally of a proximal end of the balloon and a distal end located adjacent a proximal end of a received unexpanded stent. The distal balloon control band has a proximal end located adjacent a distal end of the received unexpanded stent and a distal end located distally of a distal end of the balloon. The balloon control bands each have a diametric cross-section larger than the balloon in an uninflated state and the unexpanded stent received over the balloon to impede axial movement of the unexpanded stent off of the balloon.

19 Claims, 15 Drawing Sheets

Related U.S. Application Data division of application No. 12/969,189, filed on Dec. 15, 2010, now Pat. No. 9,061,126, which is a continuation-in-part of application No. PCT/US2010/028581, filed on Mar. 25, 2010.

(60) Provisional application No. 61/163,103, filed on Mar. 25, 2009.

(52) U.S. Cl.
CPC . *A61M 25/1034* (2013.01); *A61F 2002/9583* (2013.01); *A61M 25/0102* (2013.01); *A61M 2025/0186* (2013.01); *A61M 2025/1079* (2013.01); *A61M 2025/1093* (2013.01); *Y10T 29/4987* (2015.01); *Y10T 29/49826* (2015.01)

(58) Field of Classification Search
CPC ...... A61M 25/0102; A61M 2025/0186; A61M 2025/1079; A61M 2025/1093
USPC ........................................................ 623/1.11
See application file for complete search history.

(56) References Cited

U.S. PATENT DOCUMENTS

| | | | |
|---|---|---|---|
| 5,702,364 A | 12/1997 | Euteneuer et al. | |
| 5,810,871 A | 9/1998 | Tuckey et al. | |
| 5,968,069 A * | 10/1999 | Dusbabek | A61F 2/958 |
| | | | 604/96.01 |
| 6,071,285 A | 6/2000 | Lashinski et al. | |
| 6,174,316 B1 | 1/2001 | Tuckey et al. | |
| 6,270,504 B1 | 8/2001 | Lorentzen Cornelius et al. | |
| 6,375,660 B1 | 4/2002 | Fischell et al. | |
| 6,387,118 B1 | 5/2002 | Hanson | |
| 6,395,008 B1 | 5/2002 | Ellis et al. | |
| 6,432,130 B1 | 8/2002 | Hanson | |
| 6,562,061 B1 | 5/2003 | Wang et al. | |
| 6,585,747 B1 | 7/2003 | Limon et al. | |
| 7,033,325 B1 | 4/2006 | Sullivan | |
| 7,367,982 B2 | 5/2008 | Nash et al. | |
| 2002/0147491 A1* | 10/2002 | Khan | A61F 2/95 |
| | | | 623/1.11 |
| 2003/0033000 A1* | 2/2003 | DiCaprio | A61F 2/958 |
| | | | 623/1.11 |
| 2003/0074044 A1* | 4/2003 | Randby | A61F 2/958 |
| | | | 623/1.11 |
| 2003/0236565 A1 | 12/2003 | DiMatteo et al. | |
| 2006/0271153 A1 | 11/2006 | Garcia et al. | |
| 2008/0077223 A1 | 3/2008 | Fischell et al. | |
| 2008/0228171 A1 | 9/2008 | Kugler et al. | |
| 2008/0312671 A1 | 12/2008 | Riles et al. | |
| 2009/0281617 A1 | 11/2009 | Cottone et al. | |

OTHER PUBLICATIONS

U.S. Patent and Trademark Office Non-Final Office Action dated Dec. 18, 2012, relating to U.S. Appl. No. 13/224,037.
U.S. Patent and Trademark Office Non-Final Office Action dated Jan. 17, 2013, relating to U.S. Appl. No. 12/969,189.
European Search Report for Application No. 10756822 dated Nov. 2, 2012.

* cited by examiner

STENT DELIVERY CATHETER WITH BALLOON CONTROL BANDS

CROSS REFERENCE TO RELATED APPLICATIONS

This U.S. patent application is a continuation of, and claims priority under 35 U.S.C. §120 from, U.S. patent application Ser. No. 14/714,639, filed on May 18, 2015, which is a divisional of, and claims priority under 35 U.S.C. §121 from, U.S. patent application Ser. No. 12/969,189, filed on Dec. 15, 2010, which is a continuation-in-part of, and claims priority under 35 U.S.C. §120 and 365(c) from, PCT Patent Application PCT/US2010/028581, filed on Mar. 25, 2010, which claims priority under 35 U.S.C. §119(e) to U.S. Provisional Application 61/163,103, filed on Mar. 25, 2009. The disclosures of these prior applications are considered part of the disclosure of this application and are hereby incorporated by reference in their entireties.

TECHNICAL FIELD

This disclosure relates to medical apparatuses and specifically to a balloon catheter delivery apparatus and method for using and manufacturing the same.

BACKGROUND

Balloon deliver apparatuses, or angioplasty balloons, are useful for treating maladies in patients that involve the patients' vasculature. For example, angioplasty balloon dilation is sometimes used for the treatment of stenosis, wherein a small balloon is disposed at the location of the stenosis and inflated to expand the stenosis in a vessel lumen and improve the vessel's patency. Angioplasty balloons are also useful for deploying stents in a patient's vasculature that maintain the vessel's locally expanded state or patency and prevent restenosis. It is noted that coronary stenting is believed to reduce restenosis rates in patients when compared with conventional balloon dilation. Amer. J. Cardio. 2002, 90, 1187-1192. Fischell, et al. in U.S. Pat. Nos. 6,375,660, 6,936,065 and 7,011,673 ("the Fischell patents") show elastic bands that are placed over the ends of a stent delivery inflatable balloon that would help prevent stent embolization.

In either balloon angioplasty or stenting procedures, angioplasty balloons are typically used to expand a stenosis in a patient's vasculature. In procedures including the deployment of a stent, the angioplasty balloon may also expand and deploy the stent within the patient's vasculature. These procedures are traditionally preceded by the placement of a guidewire through the stenosis, which is followed by angioplasty balloon dilation at the stenosis with a balloon angioplasty catheter that has been advanced over the guidewire. The balloon angioplasty catheter is then withdrawn from the patient and a stent delivery system that includes the stent is advanced over the guidewire, and the stent is then deployed at the site of the dilated stenosis.

Conventional stenting procedures include the following steps:
1. Place coronary guidewire into wire introducer;
2. Load guidewire into guiding catheter;
3. Advance guidewire across lesion;
4. Remove wire introducer;
5. Load predilatation balloon angioplasty catheter onto guidewire;
6. Advance balloon catheter into guiding catheter;
7. Cross lesion with predilatation balloon;
8. Dilate lesion with balloon;
9. Angiography;
10. Remove predilatation balloon catheter;
11. Load stent delivery system (SDS) onto guidewire;
12. Advance SDS into guiding catheter;
13. Cross lesion with SDS;
14. Deploy stent at high pressure;
15. Angiography; and
16. Remove delivery system.

Because of the complexity of the procedure, conventional stenting often involves lengthy procedural times, prolonged exposure to radiation, lengthy administration of contrast agents, and great expense. J. Amer. Col. Cardio. 1999, 34, 1910-1915. Furthermore, the balloon predilation followed by stent placement often leads to major vascular trauma in a patient.

SUMMARY

The disclosure provides an apparatus and methods that improve the treatment of stenosis in a patient when compared with conventional stenting treatments. The apparatus and the methods of using the apparatus reduce vascular trauma in a patient, reduce procedural time, reduce a patient's exposure to radiation, reduce the administration of a contrast agent, and reduce costs using direct stenting procedures.

One aspect of the disclosure provides a balloon angioplasty catheter capable of delivering a balloon expandable stent where the balloon has balloon control bands that extend beyond the ends of the balloon in either or both the proximal and distal directions. It is typical for such an inflatable balloon to have five separate sections that are described as follows: 1) a central cylindrical section onto which the stent is mounted; 2) a distal cylindrical shaft that fixedly joins the balloon to the distal end of the stent delivery catheter which is typically an inner tube, which inner tube is designed to be advanced over a guide wire; 3) a distal conical section connected at its distal end to the balloon's distal cylindrical shaft and connected at its proximal end to the central cylindrical section of the balloon; 4) a proximal cylindrical shaft that fixedly joins the balloon to the distal end of an outer tube, which tube forms a lumen with a torroidal cross-section between that outer tube and the inner tube though which fluid can be introduced or removed to inflate or deflate the balloon; and 5) a proximal conical section connected at its proximal end to the to the proximal cylindrical shaft of the balloon and connected at its distal end to the central cylindrical section of the balloon.

The balloon control bands may attach to the body of the angioplasty catheter beyond the ends of the shafts of the inflatable balloon. In some implementations, the proximal balloon control band attaches to the outer tube of the stent delivery catheter at a location proximal to the proximal end of the proximal cylindrical shaft of the balloon and the distal balloon control band attach to the inner tube of the stent delivery catheter at a location distal to the distal end of the distal cylindrical shaft of the balloon. In some examples, the catheter defines a slight gap between the ends of the mounted stent and the edges of the adjacent balloon control bands. This slight gap may be needed for ease in manufacturing of the stent delivery catheter because the balloon control bands may be placed first before crimping the stent onto the central cylindrical section of the balloon between the two stent retention (balloon control) bands. Since the stent length may vary slightly, and the precision for longitudinal placement during crimping is not perfect, the manufacturing process is simplified when the distance between the inner edges of the balloon control bands is slightly longer than the longest stent that will be crimped onto the central cylindrical section of the balloon. The balloon angioplasty catheter may include a fixed wire such as is shown U.S. Pat. Nos. 6,375,660, 6,936,065 and 7,011,673, the entire contents of which are hereby incorporated by reference, or the catheter may be a rapid exchange or over-the-wire catheter having a distal end that slides over a separate guide wire.

The disclosed apparatus and methods may concern direct stenting procedures for treating stenosis. Direct stenting using the apparatus and/or methods may generally involve the following steps:

1. Placing a peel away introducer over distal end of stent delivery system;
2. Loading a stent delivery system into a guiding catheter and removing the peel away introducer;
3. Advancing the stent delivery system across lesion;
4. Dilating a balloon of the delivery system and deploying the stent at high pressure;
5. Angiography; and
6. Removing the delivery system.

Thus, direct stenting using the apparatus and/or methods offers fewer steps than conventional stenting; and consequently, procedural times are often reduced by 20-30%, the patient's radiation exposure (e.g., Fluoroscopy Time) is reduced by 20-30%, and the procedural cost is often reduced by 22-35%. Some implementations may provide some patients with a reduced incidence of restenosis and/or a reduced MACE rate. It is also noted that the omission of the predilation step in direct stenting is believed to reduce vessel wall damage and distal embolization compared with conventional stenting. See e.g., *J. Amer. Coll. Cardio.* 2008, 51, 1060-1065.

One aspect of the disclosure provides a balloon delivery catheter that includes a catheter tubing having a balloon near the distal end of the catheter tubing. The balloon includes a distal end, a proximal end, and an intermediate segment. The balloon is nested between a distal balloon control band and a proximal balloon control band. A core wire extends throughout a portion of the catheter and includes a proximal portion and a distal portion in which the distal portion of the core wire includes a coiled section that extends beyond the distal end of the balloon. In some implementations, the balloon delivery catheter further includes a stent disposed around the balloon such that when the balloon is inflated the inflated balloon expands the stent so that a radius of the stent is increased. In some examples, the catheter includes a distal balloon control band having a portion (e.g., the proximal end of the distal control band) that has a larger profile (e.g., a larger diametric cross section) than that of the unexpanded stent, so that when the balloon and stent are advanced to a stenosis site, the distal balloon control band pushes through the stenosis leaving a channel having a size sufficient for the stent. Moreover, the larger profile distal balloon control band may prevent any of the stent edges from catching on previously deployed stents thereby improving stent crossing in a patient's vasculature. In conventional catheter systems, the balloon material distal to the stent can be compressed as it is advanced into the stenosis and the distal edge of the stent can catch or engage a narrowed vessel wall or occlusion as it passes through the stenosis. These problems are advantageously avoided using the disclosed catheter, which includes a stent and a distal balloon control band having a larger profile than the stent, because the stent does not have and does not develop any exposed edges during its advancement into the stenosis. Consequently, the stent does not typically catch on the narrowed vessel walls or occlusion causing the stenosis.

Another aspect of the disclosure provides a stent delivery catheter including a catheter tubing defining a lumen therethrough, a balloon disposed near a distal end of the catheter tubing and moving between deflated and inflated states, and proximal and distal balloon control bands concentrically arranged around respective proximal and distal end portions of the balloon. The proximal balloon control band has a proximal end located proximally of a proximal end of the balloon and a distal end located adjacent a proximal end of a received unexpanded stent. The distal balloon control band has a proximal end located adjacent a distal end of the received unexpanded stent and a distal end located distally of a distal end of the balloon. The balloon control bands each have a diametric cross-section larger than the balloon in an uninflated state and the unexpanded stent received over the balloon to impede axial movement of the unexpanded stent off of the balloon.

In some implementations, each balloon control band comprises an elastic material that expands during inflation of the balloon and contracts upon deflation of the balloon. The proximal and distal balloon control bands may be secured to the respective proximal and distal end portions of the balloon. Moreover, the proximal end portion of the balloon and the proximal balloon control band can both be attached to the catheter tubing. In some examples, the proximal balloon control band is attached at least partially to the balloon and at least partially to the catheter tubing. In additional examples, the distal balloon control band is attached at least partially to the balloon and at least partially to the core wire. Each balloon control band may have a non-uniform cross-sectional thickness along an axial direction of the balloon control band. In some implementations, each balloon control band has first and second end portions. The first end portion has a larger diametric cross-section than the second end portion. Moreover, the first end portion of each balloon control band is disposed adjacent to a received stent on the balloon.

Another aspect of the disclosure provides a method of manufacturing a medical device. The method includes disposing a balloon near a distal end of a catheter tubing. The balloon is movable between deflated and inflated states. The method further includes disposing an unexpanded stent over the balloon in an uninflated state, arranging a proximal balloon control band concentrically around a proximal end portion of the balloon, and arranging a distal balloon control band concentrically around a distal end portion of the balloon. The proximal balloon control band has a proximal end located proximally of a proximal end of the balloon and a distal end located adjacent a proximal end of the unexpanded stent. The distal balloon control band has a proximal end located adjacent a distal end of the unexpanded stent and a distal end located distally of a distal end of the balloon. The balloon control bands each have a diametric cross-section larger than the balloon in an uninflated state and the unexpanded stent received over the balloon to impede axial movement of the unexpanded stent off of the balloon.

In some implementations, each balloon control band comprises an elastic material that expands during inflation of the balloon and contracts upon deflation of the balloon. The method may include at least partially securing the proximal and distal balloon control bands to the respective proximal and distal end portions of the balloon. In some examples, the method includes affixing the proximal end portion of the balloon and the proximal balloon control band both to the catheter tubing. In additional examples, the method includes shaping the balloon control bands to have a non-uniform cross-sectional thickness along an axial direction of the balloon control band. Each balloon control band has first and second end portions. The first end portion may have a larger diametric cross-section than the second end portion. The method may include arranging the first end portion of each balloon control band adjacent to a received stent on the balloon.

In yet another aspect, a method of treating vascular stenosis includes inserting into a vessel of a patient a portion of a stent delivery catheter. The stent delivery catheter includes a catheter tubing defining a lumen therethrough, a balloon disposed near a distal end of the catheter tubing and moving between deflated and inflated states, and proximal and distal balloon control bands concentrically arranged around respective proximal and distal end portions of the balloon. The proximal balloon control band has a proximal end located proximally of a proximal end of the balloon and a distal end located adjacent a proximal end of a received unexpanded stent. The distal balloon control band has a proximal end located adjacent a distal end of the received unexpanded stent and a distal end located distally of a distal end of the balloon. The balloon control bands each have a diametric cross-section larger than the balloon in an uninflated state and the unexpanded stent received over the balloon to impede axial movement of the unexpanded stent off of the balloon. The method includes advancing the balloon across the vascular stenosis, inflating the balloon to compress the vascular stenosis, deflating the balloon, and removing the stent delivery catheter from the patient.

In yet another aspect, a balloon angioplasty catheter includes a catheter tubing defining a lumen therethrough, and an inflatable balloon having a central cylindrical portion, a distal portion having a distal conical portion and a distal cylindrical shaft, and a proximal portion having a proximal conical portion and a proximal cylindrical shaft. The proximal shaft of the inflatable balloon is fixedly attached to a distal end of the catheter tubing. A balloon control band is mounted coaxially over the distal portion of the inflatable balloon. The balloon control band extends in a distal direction beyond the distal shaft of the inflatable balloon and has a proximal end located near a proximal end of the distal conical section of the balloon when the balloon is in an uninflated state.

In some implementations, the balloon angioplasty catheter includes a balloon expandable stent having a proximal end and a distal end. The stent is mounted coaxially onto the central cylindrical section of the inflatable balloon with the distal end of the stent adjacent the proximal end of the balloon control band. In some examples, a separation distance between the distal end of the stent and the proximal end of the balloon control band is less than about 2 mm. The balloon angioplasty catheter may include a fixed guide wire extending in a distal direction beyond the distal end of the distal balloon shaft. In some examples, the balloon control band has a diametric cross-section larger than the balloon in an uninflated state and an unexpanded stent received over the balloon to impede axial movement of the unexpanded stent off of the balloon. For example, a maximum outer diameter of the balloon control band may be within 1.0 mil of an outside diameter of an unexpanded stent received by the balloon. Moreover, a maximum outer diameter of the balloon control band can be between 1.0 mil and 3.0 mils greater than an outer diameter of an unexpanded stent received by the balloon.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
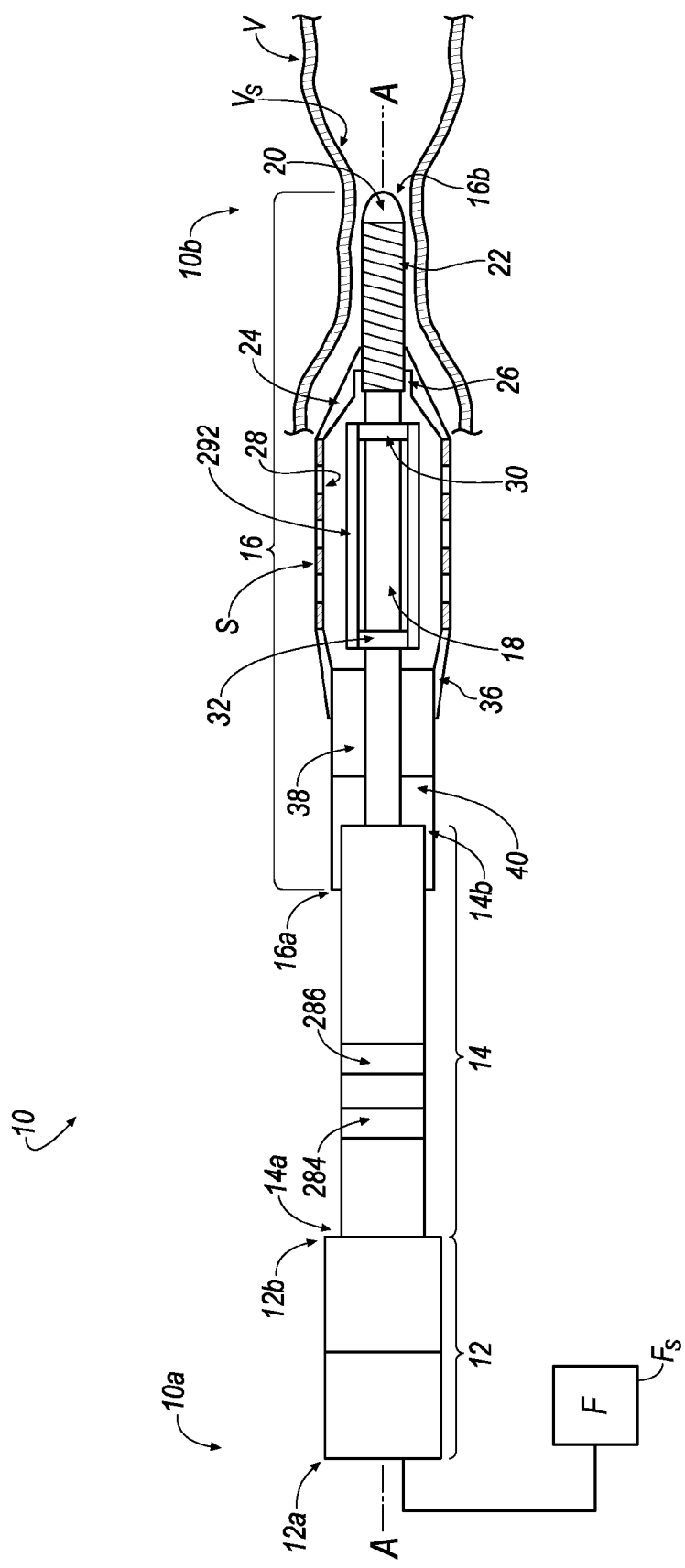
FIG. 1 is a side view of a balloon catheter delivery apparatus, in which the distal shaft portion is shown in partial longitudinal-sectional view for illustrative purposes.

The present disclosure relates generally to a balloon catheter delivery apparatus that is useful for treating stenosis in a patient.

I. Definitions

As used herein, the terms "catheter" or "catheter tubing" are used interchangeably and refer to a tube that sized and shaped to be inserted into a body cavity, duct, or vessel. Some catheters are formed of a distal portion and a proximal portion wherein the proximal portion is a hypotube, and the distal portion is a distal flexible tube. Catheters may have diameters of from about 0.3 mm to about 2.4 mm and lengths of from about 70 cm to about 170 cm.

As used herein, the terms "catheter hypotube" or "hypotube" are used interchangeably and refer to a small metallic tube that often forms the proximal portion of a catheter. Hypotubes are generally sized and shaped to be inserted into a body cavity, duct, or vessel. For example, may have outer diameters of from about 0.3 mm to about 2.4 mm, and lengths of from about 50 cm to about 140 cm (e.g., from about 70 cm to about 120 cm). Metallic hypotubes may be treated (e.g., coated, polished, sterilized, any combination thereof, or the like) to improve its utility as a portion of a catheter.

As used herein, a "distal flexible tube" is a component of a catheter located distal to a proximal portion. In some examples, the distal flexible tube has a greater flexibility than the proximal portion of the catheter. In some implementations, the distal flexible tube is formed from a polymer such as silicone rubber. In other implementations, the distal flexible tube has a diameter of from about 0.3 mm to about 2.4 mm, and a length of from about 0.5 cm to about 20 cm (e.g., from about 1 cm to about 10 cm).

As used herein, the terms "core wire" and "guide wire" are used interchangeably and refer to a small wire that extends from a distal tip of a catheter hypotube. In many instances, the distal tip of the core wire has a curved or rounded surface to inhibit its tendency to pierce or dissect a blood vessel. The term guide wire is also used in conjunction with a rapid exchange or over-the wire balloon angioplasty catheter to mean a separate wire over which the catheter is delivered.

As used herein, the term "balloon" and "balloon member" are used interchangeably and refer to a flexible inflatable container capable of increasing its volume upon inflation with a fluid and decreasing its volume upon deflation.

As used herein, "stainless steel" refers to any steel alloy with a minimum of about 10.5% chromium content by mass. It is noted that stainless steel may be coated or otherwise treated to enhance one or more of its physical properties. For instance, stainless steel may be coated with a polymer such as PTFE to reduce its coefficient of friction or improve is chemical resistance.

As used herein, "PTFE" and "polytetrafluoroethylene" are used interchangeably and refer to a synthetic fluoropolymer of tetrafluoroethylene. One such polymer is known by the DuPont brand name Teflon.

As used herein, "silicone rubber" refers to any rubber-like material composed of silicone, carbon, hydrogen, or oxygen. In several instances, silocone rubber comprises a Si—O—Si polymer backbone. Exemplary silicone rubbers include polymethylsiloxane, polyethylsiloxane, polypropylsiloxane, any combination thereof, or the like.

As used herein, "depth marker", "optical marker", and "marker" are used interchangeably and refer to optically visible marks that identify a given length or desired location on the catheter hypotube or the core wire. Some optical markers are observable in X-Ray scans of the catheter hypotube or core wire on which they are located. Other markers are optically observable by the human eye under visible light conditions. Optical markers may include painted markers or structural markers that attach to the catheter hypotube or the core wire (e.g., bands, notches, blocks, or the like).

As used herein, "affix" and "affixed" refer to the attachment of one object to another. Affixing includes bonding, welding, crimping, or otherwise adhering or attaching one object to another object.

II. Apparatus

The disclosed apparatus and methods offer several advantages over traditional balloon angioplasty and conventional stenting, for example, by providing a balloon delivery catheter that includes a catheter tubing having a balloon near the distal end of the catheter tubing. The balloon includes a distal end, a proximal end, and an intermediate segment. The balloon can be nested between a distal balloon control band and a proximal balloon control band. The catheter may include core wire extending throughout a portion of the catheter and including a proximal portion and a distal portion in which the distal portion of the core wire includes a coiled section that extends beyond the distal end of the balloon. The catheter may reduce vasculature trauma experienced by a patient when compared with conventional balloon angioplasty or conventional stenting, because the proximal and distal balloon control bands restrict longitudinal overexpansion of the balloon during inflation. This restriction in overexpansion of the balloon affected by the balloon control bands may reduce the trauma to the patient's vasculature and reduce the incidence of restenosis.

Figure 13:
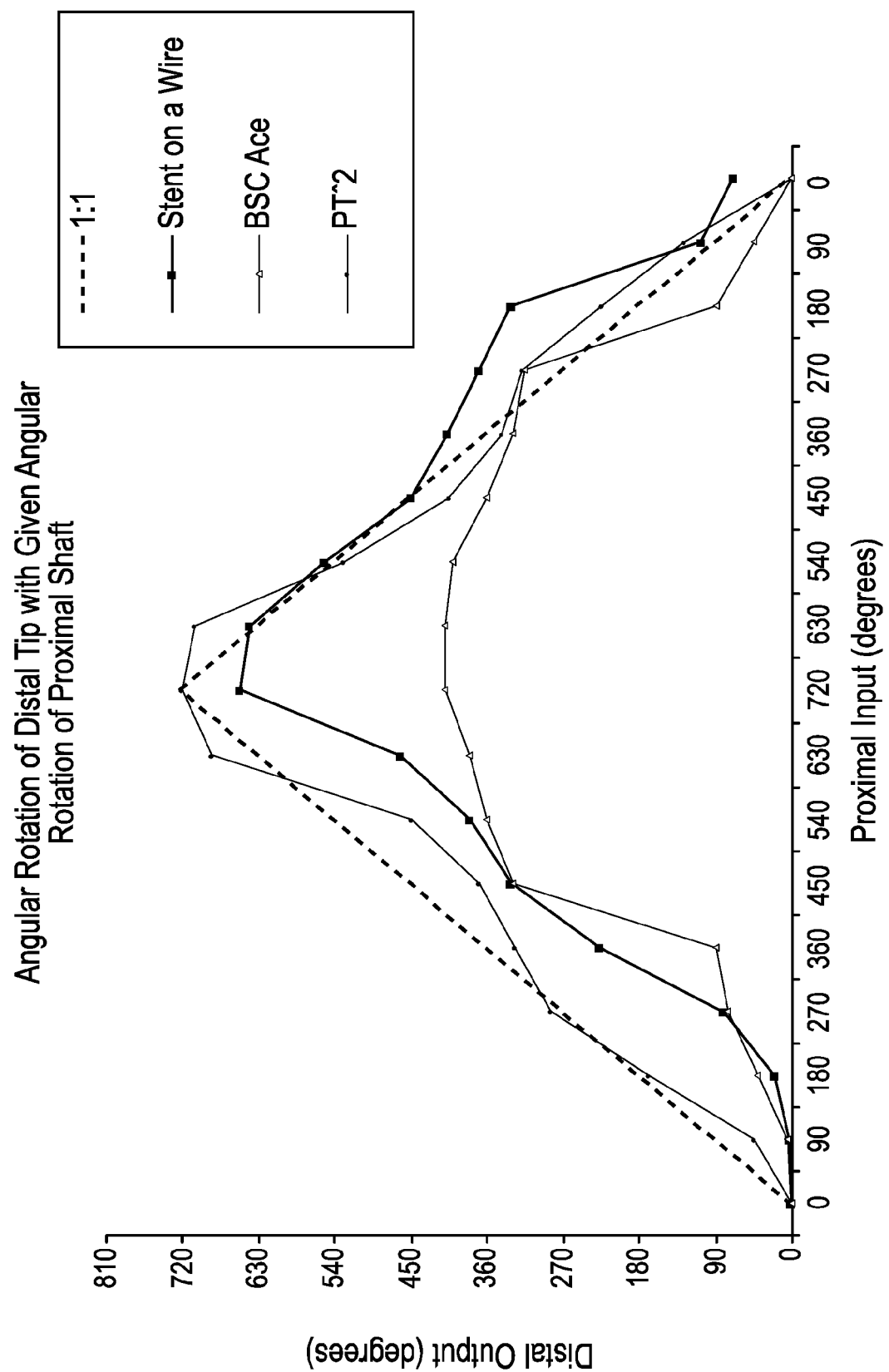
FIG. 13 is a plot of distal output (in degrees) as a function of proximal input (in degrees) for an exemplary balloon catheter delivery apparatus.
Figure 14:
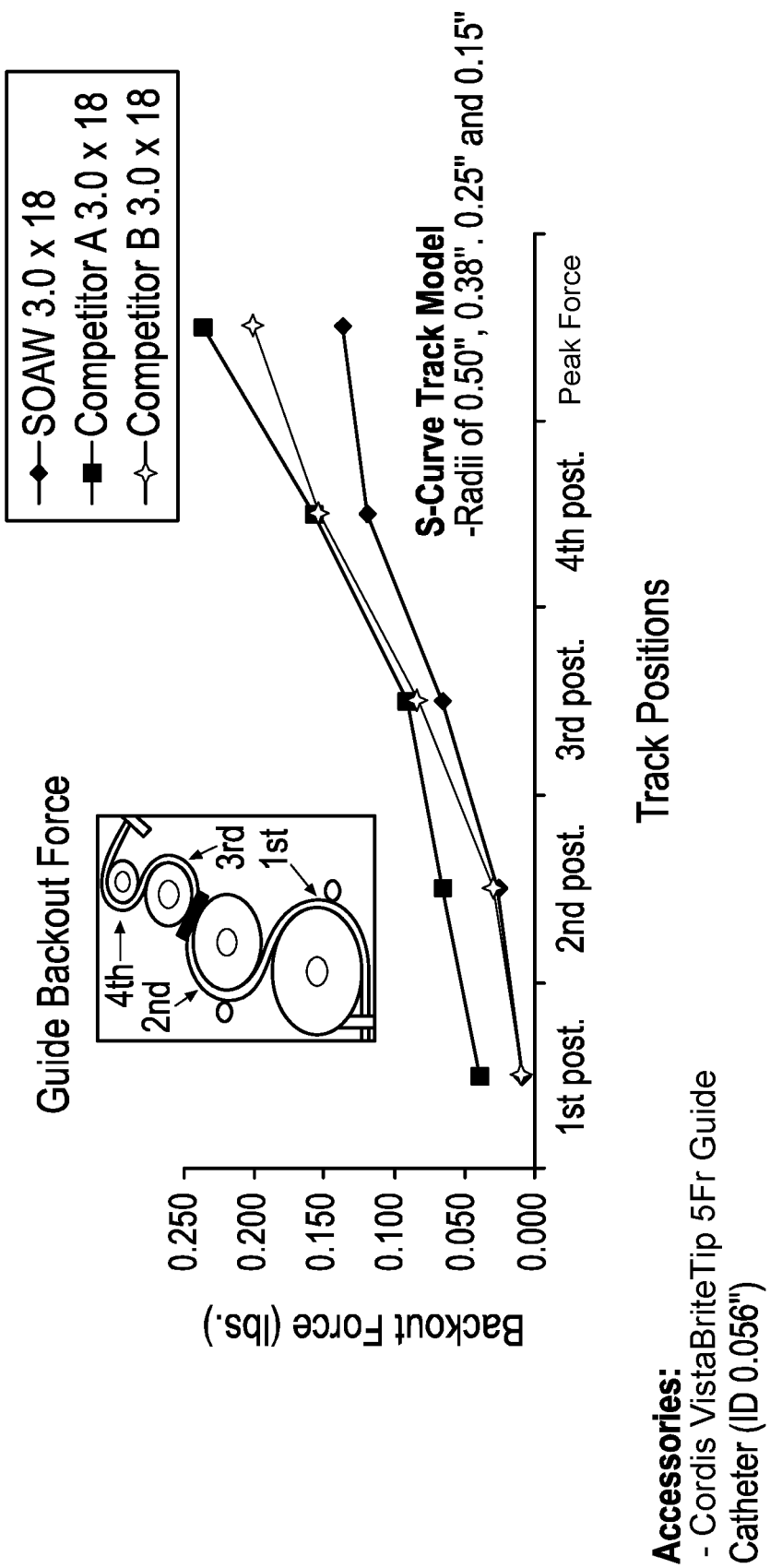
FIG. 14 is a plot of back-out force as a function of track position in an S-curve track, demonstrating that the apparatus is highly maneuverable in a patient's vasculature.

Referring to FIGS. 13 and 14, the balloon delivery catheter may provide improved control and flexibility, which provides improved maneuverability through a patient's vasculature. FIG. 13 demonstrates that the disclosed apparatus can provide excellent rotational responsiveness to a user's input rotation, and FIG. 14 demonstrates that the disclosed apparatus has excellent flexibility and can be withdrawn from bends around a series of alternating curves without the need of excessive force.

In some implementations, the balloon delivery catheter optionally includes a stent disposed around a balloon such that when the balloon is inflated, the inflated balloon expands the stent so that a radius of the stent increases. In some examples, the distal balloon control band includes at least a portion that has a greater profile, i.e., diametric cross section $DC_A$ (FIG. 12), than the unexpanded stent disposed about the balloon. These implementations may reduce the likelihood that the stent snags on a vessel wall or other occlusion at the stenosis site, because the larger profile distal control band pushes through the stenosis before the stent and creates a channel of suitable size for accepting the stent. Moreover, these implementations may reduce the likelihood that the leading edge of the stent snags on a vessel wall, a previously deployed stent, or other occlusion in the patient's vasculature, because the larger profile distal balloon control band reduces or altogether eliminates any exposed leading edges on the stent that could catch on previously deployed stents or vessel wall in a patient's vasculature. In addition, the constriction applied at the ends of the balloon by the balloon control bands retracts the balloon to a minimum diameter so that the apparatus does not snag the stent upon withdrawal of the apparatus from the patient.

In some implementations, a balloon delivery catheter apparatus includes an all-in-one stent delivery system comprising a fixed guide wire and a catheter including an elongate flexible hypotube having distal and proximal shaft portions and an inflatable balloon to which a stent may optionally be affixed thereto. The balloon may be in fluid communication with the lumen of the flexible hypotube. In some examples, the proximal end of the core wire is affixed to the distal end of the proximal shaft portion of the catheter hypotube and the distal tip of the core wire extends beyond the balloon. The balloon has a proximal end attached to the distal section of the hypotube and a distal end attached to the core wire at a location proximal to the distal tip of the wire.

The apparatus may include balloon control bands that assist in stent deployment and/or vessel expansion by constricting dilation of the balloon at its proximal and distal ends, thereby encouraging the balloon midsection beneath the stent (if a stent is affixed to the balloon) to inflate and deploy at the middle before the ends expand. In embodiments comprising the optional stent, the balloon control bands restrict the overexpansion of the balloon and the stent affixed thereto at their respective ends—an event that often causes trauma to vessel walls. This restriction in overexpansion of the balloon caused by balloon control bands may reduce the incidence of restenosis in the patient. In addition, the constriction applied at the ends of the balloon by the balloon control bands retracts the balloon to a minimum diameter so that the apparatus does not snag the stent upon removal from the patient. In various examples, the profile of the apparatus may be minimized not only by the balloon control bands, but also by the various connections within the apparatus, many of the components being directly bonded to one another, for example, but not limited to, laser welding.

FIG. 1 provides a part side view, part longitudinal-sectional illustrative view of a balloon catheter delivery apparatus 10, which may also be referred to as a stent-on-a-wire (SOAW) delivery catheter. In some examples, the delivery apparatus 10 may be sterilized by an ethylene oxide gas, radiation treatment (e.g., treatment with e-beam or gamma radiation), sterilizing solution, any combination thereof, or other sterilizing medium or procedure compatible with the materials used in the balloon catheter delivery apparatus.

Although the foregoing description discloses a balloon catheter delivery apparatus 10 that may be used for placing a stent S at, for example, a stenosis $V_S$ of a vessel V in, for example, a patient, (e.g., a human), other uses are possible. Accordingly, in some implementations, the delivery apparatus 10 may be utilized to treat, for example, ischemic heart disease. Further, the delivery apparatus 10 may also find utility as an angioplasty catheter that does not include a stent S or the stent S may be removably affixed to the balloon catheter delivery apparatus 10.

The delivery apparatus 10 may be used for placing an angioplasty balloon catheter through a stenosis $V_S$. The structure of delivery apparatus 10 may enhance, for example, the pushability of an angioplasty catheter that is utilized for dilating a stenosis $V_S$.

Figure 11:
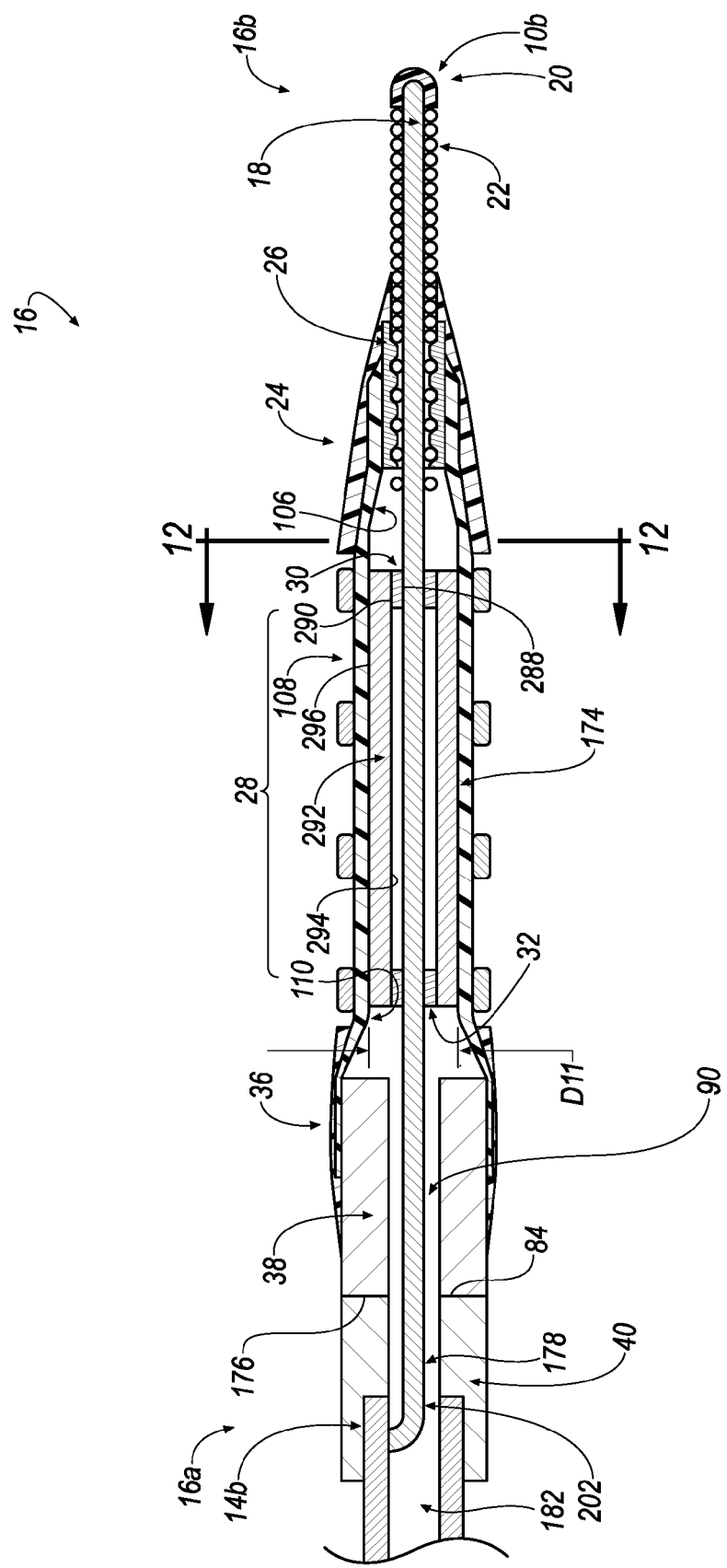
FIG. 11 is a longitudinal-sectional view of a distal shaft portion of the balloon catheter apparatus in an undeployed state.
Figure 12:
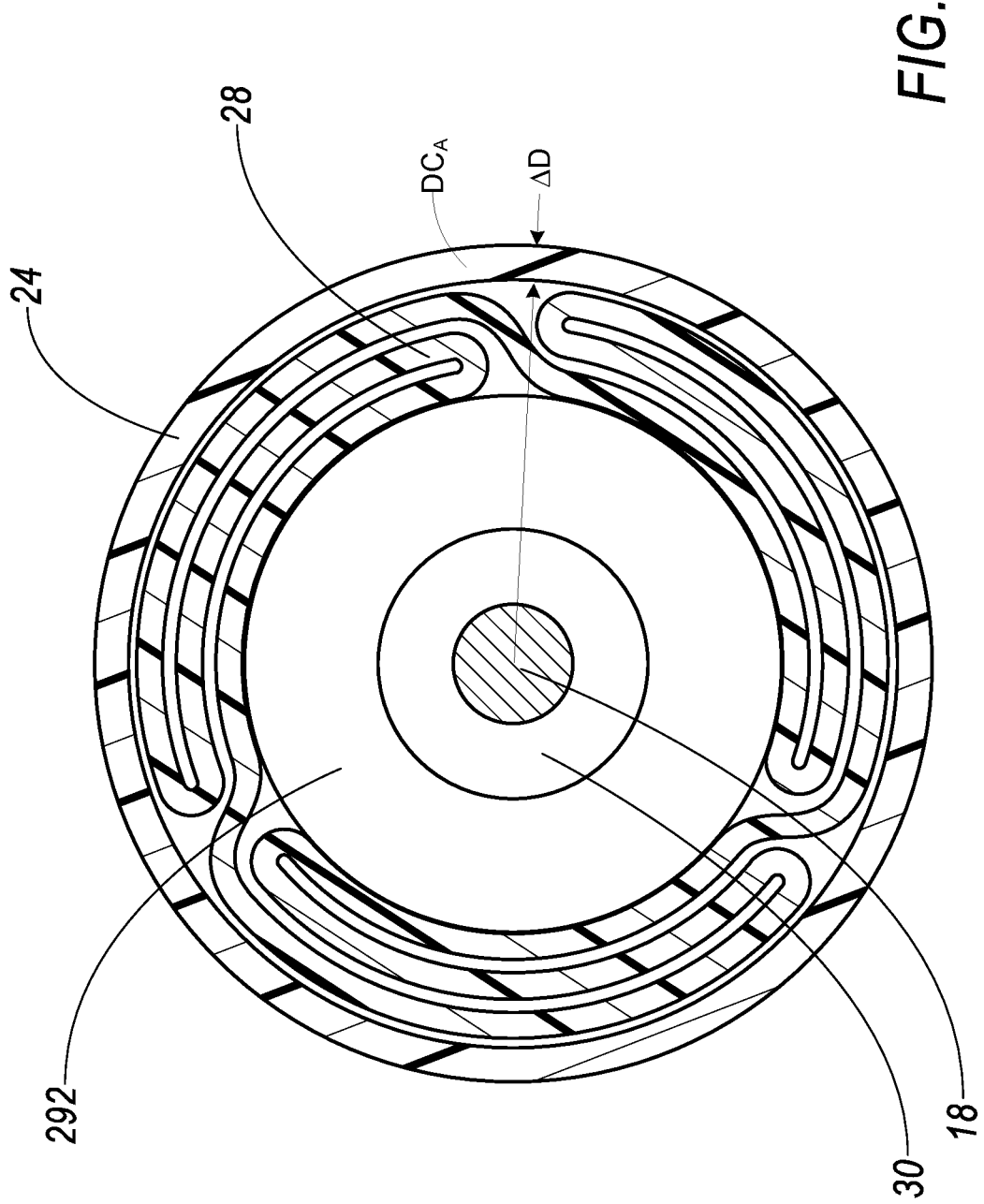
FIG. 12 is a cross-sectional illustration of the distal shaft taken at about line 12 of FIG. 11 and viewed in a proximal direction in accordance with an example embodiment of the invention.

A distal shaft portion 16 of the delivery apparatus 10 is shown in a slightly expanded or inflated state in the examples shown in FIGS. 1-7. The examples shown in FIGS. 11 and 12 illustrate the distal shaft portion 16 of the delivery apparatus 10 prior to inflation.

As seen in FIG. 1, an axis A-A extends through the delivery apparatus 10 from a proximal end 10a to a distal end 10b. The delivery apparatus 10 may optionally include a handle 12 having a proximal end 12a and a distal end 12b. The delivery apparatus 10 may also include a catheter hypotube that comprises a proximal shaft section 14 having a proximal end 14a and a distal end 14b. The catheter hypotube also comprises a proximal distal shaft portion 16 having a proximal end 16a and a distal end 16b.

The handle 12, the proximal shaft portion 14, and/or all or part of the distal shaft portion 16 may form a lumen or passage allowing for inflation of a balloon 28 of the delivery apparatus 10. The proximal end 14a of the proximal shaft portion 14 may be fixedly or removably connected to the distal end 12b of the handle 12. In some examples, the distal end 12b of the handle 12 is approximately 145 centimeters from the distal end 10b of the delivery apparatus 10.

Moreover, the distal end 14b of the proximal shaft portion 14 may be fixedly or removably connected proximate to the proximal end 16a of the distal shaft portion 16. In some examples, the distal end 14b of the proximal shaft portion 14 is disposed within the distal shaft portion 16 proximate to the proximal end 16a of the distal shaft portion 16 (see e.g., FIG. 4). Alternatively, the proximal end 16a of the distal shaft portion 16 may be disposed within the distal end 14b of the proximal shaft portion 14. Other ways of connecting the handle 12, the proximal shaft portion 14 and the distal shaft portion 16 are possible as well.

In some implementations, the delivery apparatus 10 functions in a manner that permits the stent, S, to be removably attached to the distal shaft portion 16. Further, the distal shaft portion 16 may retain the stent S and later deploy the stent S at, for example, a stenosis $V_S$ of a vessel V of a human body. Upon deployment of the stent S, the delivery apparatus 10 may be said to no longer include or retain the stent S.

The handle 12 and the proximal shaft portion 14 may function in a manner that permits communication of a fluid F from a fluid source $F_S$ to the distal shaft portion 16. In some examples, the handle 12 functions in a manner that permits or denies movement of the fluid F into or out of the distal shaft portion 16 by way of the proximal shaft portion 14. The fluid F may be pressurized to between about 8 and about 16 atmospheres.

Figure 2:
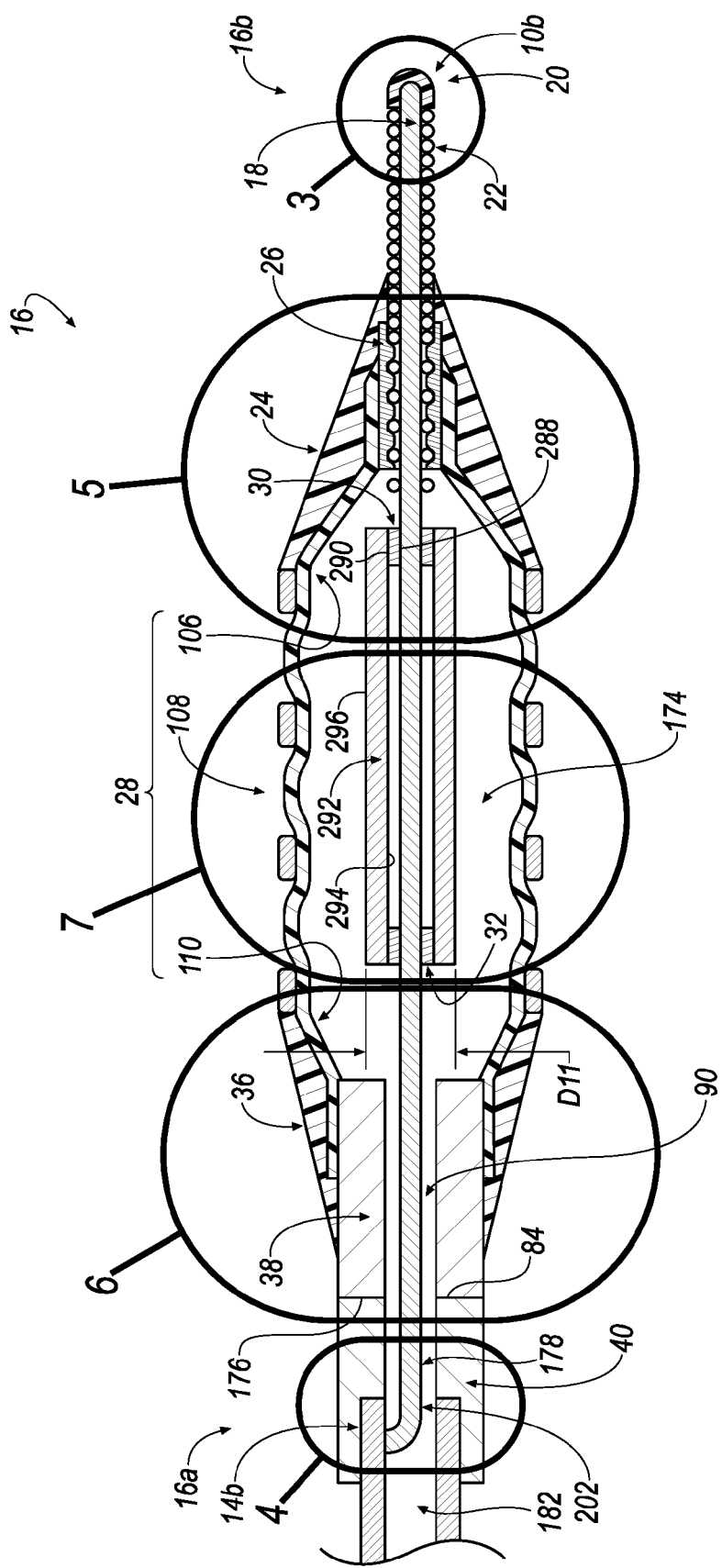
FIG. 2 is a longitudinal-sectional view of a distal shaft portion of the balloon catheter delivery apparatus of FIG. 1.

Referring to FIGS. 1 and 2, in some implementations, the distal shaft portion 16 includes an axial core wire 18, a capped distal tip member 20, a coil member 22, a distal balloon control band 24, a distal bonding portion 26, a balloon 28, a distal marker band 30, a proximal marker band 32, a proximal balloon control band 36, a distal shaft mounting portion 38 and a proximal shaft mounting portion 40.

Figure 4:
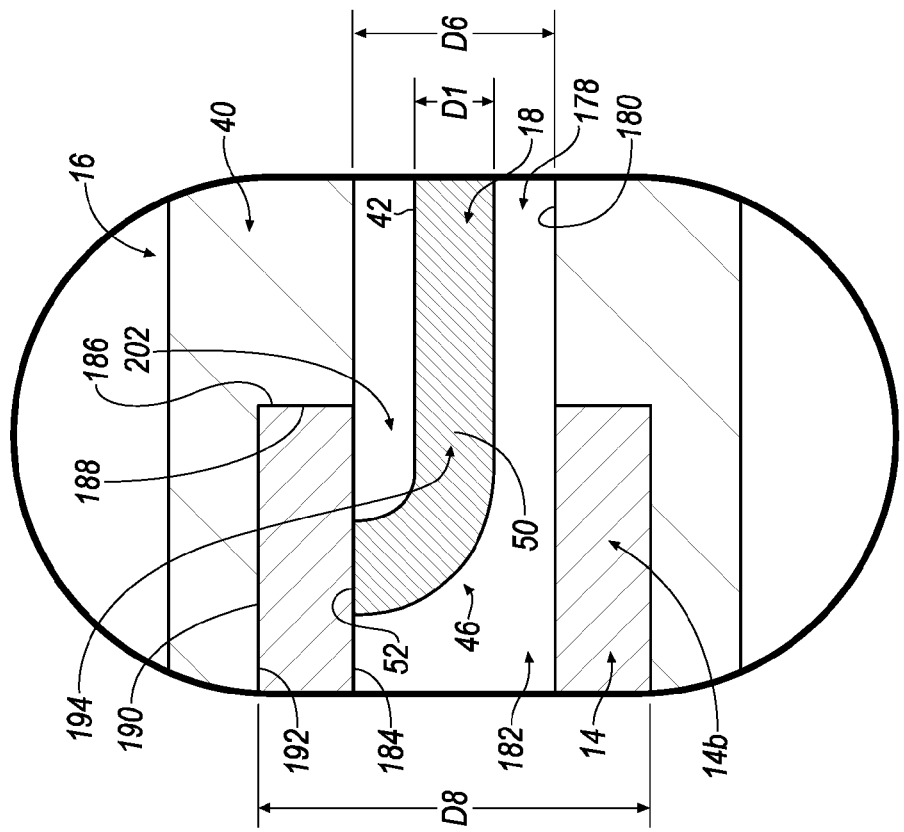
FIG. 4 is an enlarged view of a portion of the distal shaft portion indicated by line 4 of FIG. 2.
Figure 3:
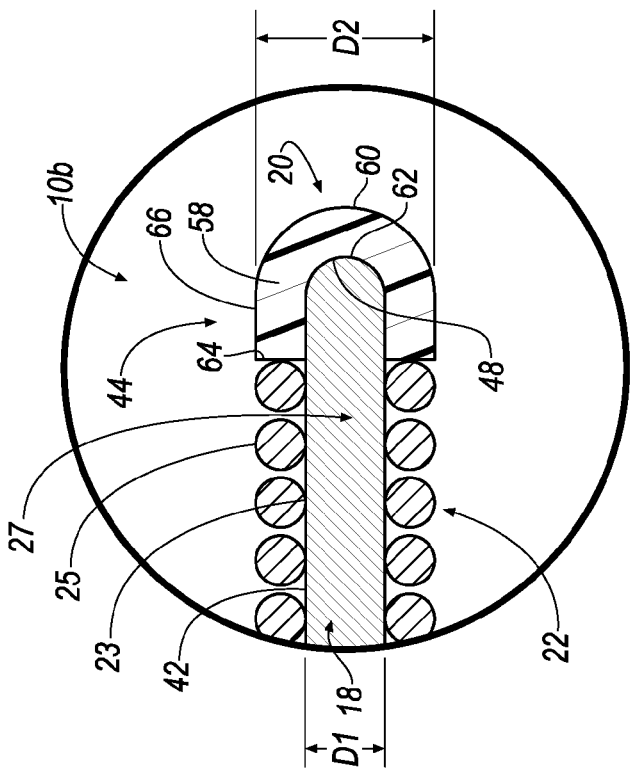
FIG. 3 is an enlarged view of a portion of the distal shaft portion indicated by line 3 of FIG. 2.

Referring now to FIGS. 3 and 4, the core wire 18 may include a radial outer surface 42, a first, axial distal end segment 44 and a distal end surface 48 (see e.g., FIG. 3) and a second, axial proximal end segment 46 and a distal end surface 52 (see e.g., FIG. 4). As shown in FIGS. 1 and 2, in some examples, the distal end segment 44 of the core wire 18 may extend beyond the distal end of the balloon control band 24.

The radial outer surface 42 may define the core wire 18 to include a substantially circular cross-section having an outer diameter D1. The radial outer surface 42 is not limited, however, to defining the core wire 18 to include a substantially circular cross section and the core wire 18 may include any desirable cross-sectional shape, such as, for example, a square, rectangular, hexagonal cross-section or the like. In addition, the shape of the core wire 18 may not be uniform. For example, a portion of the core wire 18 within the capped distal tip member 58 may be substantially circular, while a portion of the core wire 18 that lies within the coil member 22 may be rectangular. The core wire 18 may taper as it extends axially from the proximal end 10a to the distal end 10b. The core wire 18 may also be coined. The tapering and coining of the core wire 18 may permit the core wire 18 to be flexible and/or shapeable.

As seen in FIGS. 2 and 3, the first axial, distal, end segment 44 of the core wire 18 may define, in part, a distal end 10b of the delivery apparatus 10. The first, axial distal end segment 44 may terminate in a rounded, substantially dome-shaped distal end surface 48. As seen in FIGS. 2 and 4, the second axial, proximal, end segment 46 of the core wire 18 may be located axially away from the distal end 10b of the delivery apparatus 10 at any desirable axial distance/ length. The second axial proximal end segment 46 may terminate in a proximal end surface 52. The proximal end surface 52 may be connected directly to an inner wall 184 of the proximal shaft portion 14 by any suitable method, such as, but not limited to, laser welding.

Referring to FIG. 3, in some implementations, the capped distal tip member 20 defines, in part, the distal end 10b of the delivery apparatus 10. For example, the capped distal tip member 20 may be formed from or an integral part of the core wire 18, or, alternatively, the capped distal tip member 20 may be formed as a separate component, as illustrated, from that of the core wire 18.

The capped distal tip member 20 may define a cup-shaped body 58 having a substantially U-shaped longitudinal section. The cup-shaped body 58 may include a distal, dome-shaped outer axial surface 60 and a proximal, recessed axial surface 62 that corresponds to and may be axially disposed adjacent the rounded, substantially dome-shaped axial/distal end surface 48 of the core wire 18. In some examples, the recessed axial surface 62 is heat-bonded with the axial/distal end surface 48 of the core wire 18. In additional examples, the distal portion of the core wire 18 is melted, with a laser welder or by other suitable means, to form the integral capped distal tip member 20.

The proximal, recessed axial surface 62 of the capped distal tip member 20 may extend axially toward the proximal end 10a of the delivery apparatus 10 to define a substantially annular (in cross-section) axial proximal end surface 64 around the radial outer surface 42 of the core wire 18. The substantially annular axial proximal end surface 64 may extend to an outer radial side surface 66 that extends to the distal, dome-shaped outer axial surface 60. The connection of the substantially annular, axial end surface 64 and the outer radial side surface 66 may define a diameter D2 of the capped distal tip member 20. In some examples, the diameter D2 may be greater than the diameter D1 of core wire 18.

The coil member 22 may be composed of, but is not limited to, a platinum-iridium (Pt/Ir) material in whole or in part. As shown in FIG. 3, the coil member 22 may generally define an inner surface 23 and an outer surface 25. In some examples, the inner surface 23 defines a passage 27 with a diameter that is approximately the same as, but slightly greater than the diameter D1 of core wire 18, to permit the core wire 18 to extend through the passage 27 so that the coil member 22 may be arranged concentrically relative to the core wire 18. Moreover, the coil member 22 may be radiopaque.

Figure 5:
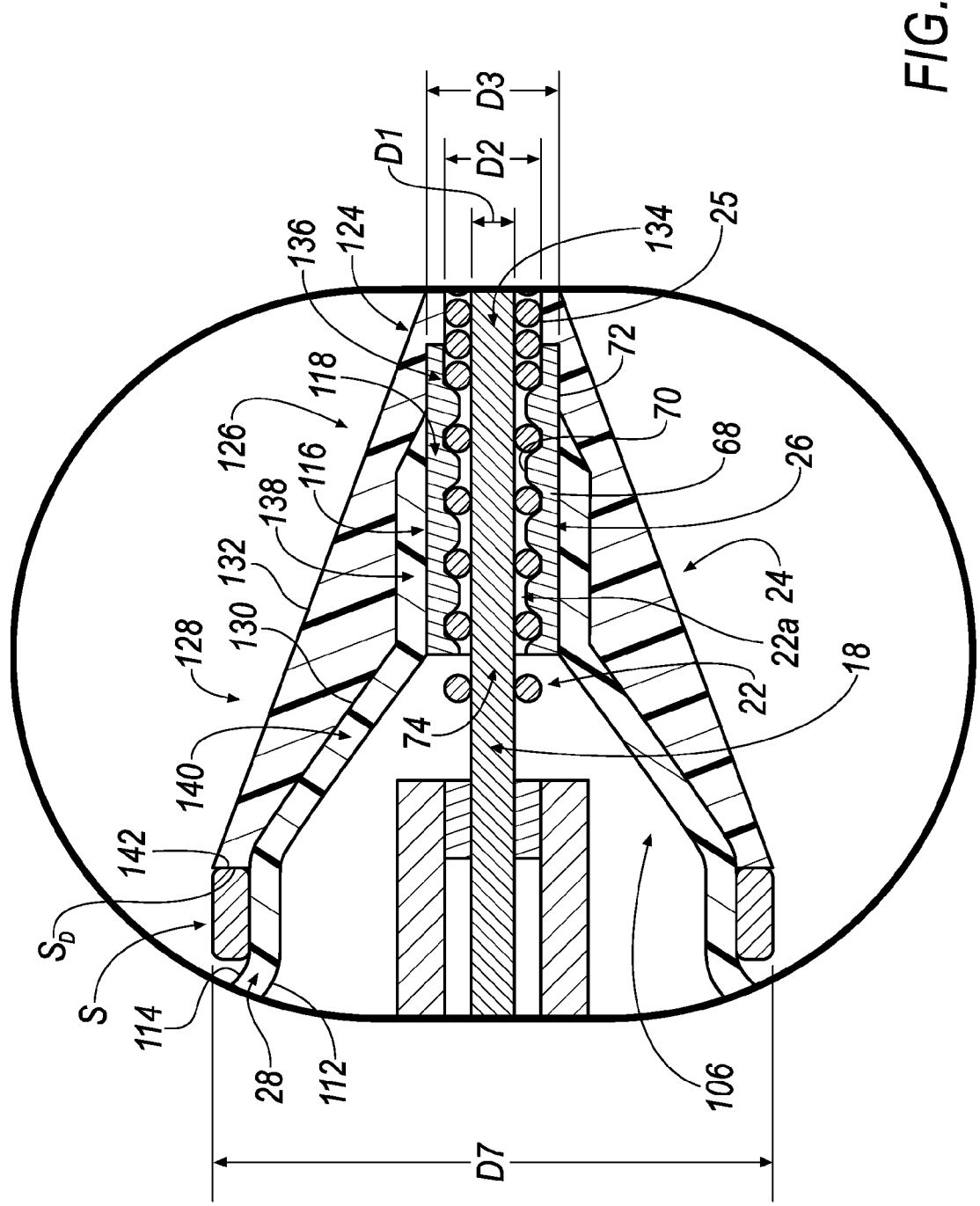
FIG. 5 is an enlarged view of a portion of the distal shaft portion indicated by line 5 of FIG. 2.

The outer surface 25 of the coil member 22 may define the coil member 22 to have an outer diameter substantially equal to or less than the diameter D2 of the capped distal tip member 20. The outer diameter D2 of the coil member 22 may be approximately, but is not limited to, 0.012 inches. In some examples, the coil member 22 has any desirable axial length, for instance, but not limited to, approximately 22 millimeters. As shown in FIG. 5, in some implementations, the proximal portion of the coil member 22 may be stretched to create a series of spaces 22a between individual coils.

Referring back to FIGS. 2 and 3, the coil member 22 may be disposed substantially adjacent to either of or both of the radial outer surface 42 of the core wire 18 and the substantially circular, axial end surface 64 of the capped distal tip member 20. The coil member 22 may be fixedly connected or joined to one or more of the radial outer surface 42 and the substantially annular, axial end surface 64. The coil member 22 may be connected or joined to either or both surfaces 42, 64 via any suitable methodology such as, for example, a laser-welding operation. In some examples, the outer surface 25 of the coil member 22 is heat-bonded with an inner surface 130 of the distal balloon control band 24, shown in FIG. 5. The inner surface 130 of the distal balloon control band 24 may extend into the spaces 22a (not shown).

The cup-shaped body 58 of the capped distal tip member 20 may help to functionally prevent the coil member 22 from axially moving and/or radially separating (i.e., uncoiling) along the core wire 18. Further, the geometry of the rounded, dome-shape surface 60 of the capped distal tip 20 may functionally provide the delivery apparatus 10 with a radiused, atraumatic tip.

Referring to FIG. 5, the distal bonding portion 26 may include, but is not limited to, a substantially cylindrical body, sleeve or tube 68 having an inner radial surface 70 and an outer radial surface 72. The outer radial surface 72 may define a diameter D3. The inner radial surface 70 may define a diameter that may be approximately the same as, but slightly greater than diameter D2 (see e.g., FIG. 3).

The distal bonding portion 26 may include a low-density polyethylene (LDPE) material or the like. In some examples, the distal bonding portion 26 is utilized to bond the coil member 22 with one or more of the balloon 28 and the distal balloon control band 24, which may prevent twisting of the balloon 28 on the core wire 18. Bonding between other components, such as the coil member 22 and the distal balloon control band 24 and the distal bonding portion 26 or other reshaping of the bonding portion 26 may be activated by, for example, treatment of the bonding portion 26 with a laser. The distal bonding portion 26 may extend into the spaces 22a. In some examples, the coil member 22 is stretched to permit the distal bonding portion 26 to extend into the spaces 22a.

The substantially cylindrical tube 68 may be concentrically arranged relative to the core wire 18 and the coil member 22 such that one or more of the core wire 18 and the coil member 22 extends through a passage 74 defined by the inner radial surface 70 of the substantially cylindrical tube 68 of the distal bonding portion 26. The inner radial surface 70 may be disposed adjacent to the outer radial surface 25 of the coil member 22.

Figure 6:
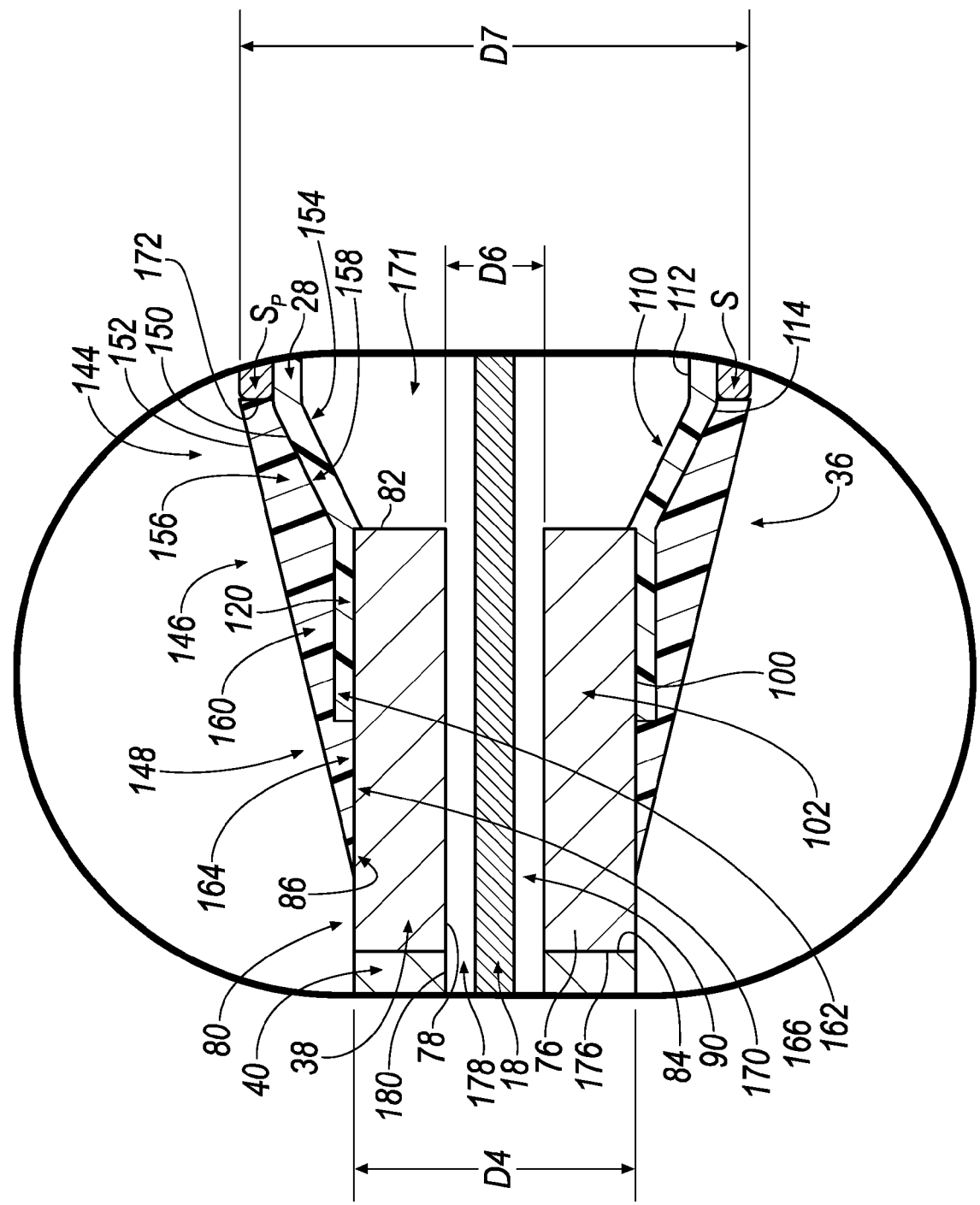
FIG. 6 is an enlarged view of a portion of the distal shaft portion indicated by line 6 of FIG. 2.

Referring to FIG. 6, one or more of the distal shaft mounting portion 38 and the proximal shaft mounting portion 40 may include, but are not limited to, a polymeric material such as a polyamide material. A proximal end of the distal shaft mounting portion 38 may be heat-bonded to a distal end of the proximal shaft mounting portion 40. Although the distal and proximal shaft mounting portions 38, 40 may include a polymeric material in some embodiments, the durometer (i.e., the hardness/softness) of the polymeric material may not necessarily be the same between or within the shaft mounting portions 38, 40. For instance, the hardness/softness of the proximal shaft portion 14, proximal shaft mounting portion 40, and the distal shaft mounting portion 38 can each be selected such that the proximal shaft portion 14 is more rigid than the proximal shaft mounting portion 40 and the distal shaft mounting portion 38, and the proximal shaft mounting portion 40 is more flexible than the proximal shaft portion 14, but less flexible than the distal shaft mounting portion 38. In this configuration, the proximal shaft portion 14 provides rigidity to the apparatus and the proximal shaft mounting portion 40 and the distal shaft mounting portion 38 provide sufficient flexibility to navigate coronary or other vessel anatomy as the distal shaft portion 16 is positioned for deployment.

Figures illustrating the proximal shaft portion 14, the proximal shaft mounting portion 40, the distal shaft mounting portion 38 and the distal shaft portion 16 are not drawn to scale and are merely a convenient representation of those components. The relative lengths of these components can vary as necessary to provide an apparatus that can be used to navigate coronary or other vessel anatomy. For instance, the relative lengths of proximal shaft mounting portion 40 and the distal shaft mounting portion 38 can be approximately 15 centimeters and 35 centimeters, respectively.

As illustrated in FIG. 6, the distal shaft mounting portion 38 may include, but is not limited to, a substantially cylindrical body, sleeve or tube 76 having an inner radial surface 78 and an outer radial surface 80, an axial distal end surface 82 and an axial proximal end surface 84. A passage 90 that may be defined by the inner radial surface 78 may have an inner diameter D6 that extends axially through the distal shaft mounting portion 38 from the axial proximal end surface 84 to the axial distal end surface 82. The distal shaft mounting portion 38 may be concentrically arranged relative to the core wire 18 such that the core wire 18 axially extends through the passage 90.

In some embodiments, a proximal portion of the proximal balloon control band 36 is bonded to the outer radial surface 80 of a distal end of the distal shaft mounting portion 38, by any suitable method, such as by laser welding. The area of the outer radial surface covered by the proximal portion of the proximal balloon control band 36, i.e., area 86, may extend part or all of the way over the outer radial surface 80 of distal shaft mounting portion 38. The distal portion of proximal balloon control band 36 may extend radially around the proximal portion of balloon 28. The distal portion of the proximal balloon control band 36 may be made of a material that will stretch as axial chamber 174 as defined by balloon 28 is inflated and snap back or relax into its initial position when axial chamber 174 as defined by balloon 28 is deflated, thereby helping to collapse the balloon 28 and minimize the profile of the apparatus following balloon 28 deflation. In some examples, a proximal bonding portion may secure the proximal balloon control band 36 to the distal end of the distal shaft mounting portion 38 (not shown).

Referring to FIGS. 2 and 5-7, the balloon 28 may include, but is not limited to, for example, a nylon material. The balloon 28 may include a distal segment 106 (see e.g., FIG. 5), an intermediate segment 108 (see e.g., FIG. 7) and a proximal segment 110 (see e.g., FIG. 6) collectively defining an inner surface 112 and an outer surface 114 of the balloon 28.

Referring to FIG. 5, in some implementations, a portion 116 of the inner surface 112 of the distal segment 106 of the balloon 28 may be arranged adjacent to a portion 118 of the outer radial surface 72 of the distal bonding portion 26. Similarly, referring to FIG. 6, in some implementations, a portion 120 of the inner surface 112 of the proximal segment 110 of the balloon 28 may be arranged adjacent to the outer radial surface 80 of the distal shaft mounting portion 38. The inner surface 112 of the portion 120 of the balloon 28 may be bonded to the distal end of distal shaft mounting portion 38, by, for instance, but not limited to laser welding, thereby minimizing the profile of apparatus 10.

With further reference to FIG. 5, the distal balloon control band 24 may include a distal segment 124, an intermediate segment 126 and a proximal segment 128 that collectively define an inner surface 130 and an outer surface 132 of the distal balloon control band 24. In some examples, the outer surface 132 of distal balloon control band 24 generally defines the distal balloon control band 24 to form a conical outer surface tapering in the distal direction.

The distal segment 124 of the distal balloon control band 24 may be arranged concentrically with respect to the core wire 18 and the coil member 22. The inner surface 130 may define the distal balloon control band 24 to include a passage 134 that permits one or more of the core wire 18, the coil member 22, the distal bonding portion 26, and the balloon 28 to axially extend through the distal control band 24.

The passage 134 may include a constant or a non-constant diameter (e.g., creating a tapering, widening, constricting, and/or expanding passage 134) for one or more of the segments 124, 126, and 128. For instance, the passage 134 may decrease in diameter, as shown in FIG. 5, as the distal balloon control band 24 extends from the proximal end 10a toward the distal end 10b of the delivery apparatus 10.

In some examples, one or more of the core wire 18, the coil member 22 and the distal bonding portion 26 axially extend through the passage 134 proximate to one or more of the distal segment 124 and the intermediate segment 126 of the distal balloon control band 24. The inner surface 130 of the distal segment 124 of the distal balloon control band 24 may be disposed substantially adjacent and attached to one or more of the outer surface 25 of the coil member 22 and a portion 136 of the outer surface 72 of the distal bonding portion 26.

The intermediate segment 126 of the distal balloon control band 24 may be arranged concentrically with respect to one or more of the core wire 18, the coil member 22, the distal bonding portion 26 and a portion of the distal segment 106 of the balloon 28. The inner surface 130 of the intermediate segment 126 of the distal balloon control band 24 may be disposed adjacent to a portion 138 of the outer surface 114 of the distal segment 106 of the balloon 28. The portion 138 can be referred to as a distal step portion or a distal tubular portion of the balloon 28.

The proximal segment 128 of the distal balloon control band 24 may be arranged concentrically with respect to one or more of the core wire 18, a portion of the axial length of the coil member 22, and a portion of the distal segment 106 of the balloon 28. The inner surface 130 of the proximal segment 128 of the distal balloon control band 24 may be disposed adjacent to a portion 140 of the outer surface 114 of the distal segment 106 of the balloon 28. The portion 140 may be referred to as a distal ramp portion or distal conical portion of the balloon 28. The distal conical portion 140 may be connected to the distal tubular portion 138 of the balloon 28.

Referring to FIG. 6, the proximal balloon control band 36 may include a distal segment 144, an intermediate segment 146 and a proximal segment 148 collectively defining an inner surface 150 and an outer surface 152. The outer surface 152 of the proximal balloon control band 36 may define the proximal balloon control band to include a proximal outer conical portion, tapering in the proximal direction.

The distal segment 144 of the proximal balloon control band 36 may be arranged concentrically with respect to one or more of the core wire 18 and a portion 154 of the balloon 28. A portion 156 of the inner surface 150 of the proximal balloon control band 36 may be disposed substantially adjacent and attached to a portion 158 of the outer surface 114 of the proximal segment 110 of balloon 28. The portion 158 can be referred to as a proximal ramp portion or the proximal conical portion of the balloon 28.

Intermediate segment 146 of the proximal balloon control band 36 may be arranged concentrically with respect to one or more of the core wire 18, the distal shaft mounting portion 38 and the proximal segment 110 of the balloon 28. A portion 160 of the inner surface 150 of the proximal balloon control band 36 may be disposed adjacent a portion 162 of the outer surface 114 of the proximal segment 110 of the balloon 28. The portion 162 can be referred to as a proximal tubular portion of the balloon 28. The proximal conical portion 158 of the balloon 28 may be connected to the proximal tubular portion 162 of the balloon 28.

The proximal segment 148 of the proximal balloon control band 36 may be arranged concentrically with respect to one or more of the core wire 18, a portion 120 of the balloon 28, and a portion 170 of the distal shaft mounting portion 38. A portion 164 of the inner surface 150 of the proximal segment 148 of the proximal balloon control band 36 may be disposed substantially adjacent to the portion 170 of the outer radial surface 80 of the distal shaft mounting portion 38.

The proximal balloon control band 36 may define an axial passage 171 that permits one or more of the core wire 18, the proximal segment 110 of the balloon 28, and the distal shaft mounting portion 38 to axially extend therethrough. Further, the passage 171 may include a constant or non-constant diameter for one or more segments 144, 146, 148 of the proximal balloon control band 36 and/or may increase in diameter as the proximal balloon control band 36 extends from the proximal end 10a toward the distal end 10b of the delivery apparatus 10.

The proximal control bands 36 and distal balloon control bands 24 may apply pressure to the proximal segments 110 and the distal segment 106 of the balloon 28. When fluid F moves into the balloon 28, causing dilation of the balloon 28, the pressure applied by the proximal and distal balloon control bands 36, 24 at the proximal and distal segments 110, 106 of the balloon 28 encourages inflation at the intermediate segment 108 of the balloon 28 first relative to the ends. This improves uniform stent deployment by promoting uncrimping of the stent S at its middle rather than at the distal and proximal ends of the stent S, thereby minimizing over expansion at the ends of the stent S and/or preventing vessel tissue trauma distal and/or proximal to the deployed stent S and area of stenosis. In addition, the pressure applied by the proximal and distal balloon control bands 36, 24 to the proximal and distal segments 110, 106 of the balloon 28 may assist with balloon deflation after stent deployment. As the fluid F is removed from the apparatus 10, the pressure applied by the balloon control bands 36, 24 assists in collapsing the proximal and distal balloon segments 110, 106. This minimizes the profile of the balloon 28 so that it can be removed from the vessel V without snagging the vessel wall or the deployed stent S.

Figure 7:
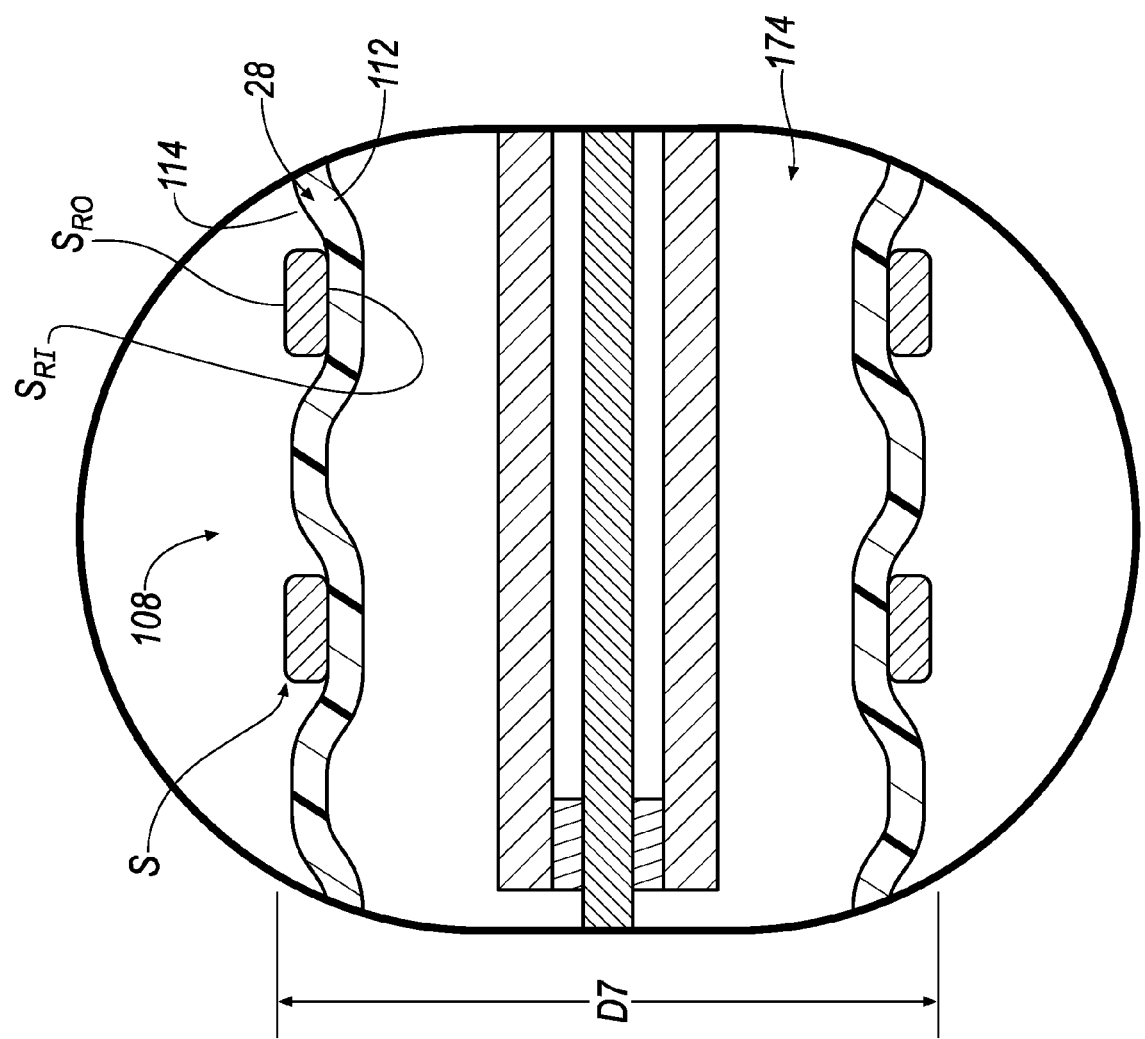
FIG. 7 is an enlarged view of a portion of the distal shaft portion indicated by line 7 of FIG. 2.

FIG. 7 depicts an exemplary intermediate segment 108 of the balloon 28 and a portion of the stent S. In some implementations, the stent S defines an inner radial surface $S_{RI}$ and an outer radial surface $S_{RO}$. The inner radial surface $S_{RI}$ of stent S may be disposed/stowed substantially adjacent to the outer surface 114 of the balloon 28 before/during the axial carrying/delivery of the stent S within the vessel V. In some examples, the inner radial surface $S_{RI}$ of the stent S is crimped onto the outer surface 114 of the balloon 28.

The intermediate segment 108 of the balloon 28 may also be referred to as an intermediate tubular portion of the balloon 28. The outer surface 114 of the intermediate tubular portion 108, taken together with the outer surface $S_{RO}$ of stent S may have a generally constant diameter D7. The intermediate tubular portion 108 may be arranged between and connect the distal and proximal conical portions of the balloon 28.

The balloon 28 may be expanded from a retracted orientation as shown in the figures to an expanded/inflated orientation (not shown). The expansion/inflation of the balloon 28 may be caused by the received fluid F (see e.g., FIG. 1), which may be moved into an axial chamber 174 of the balloon 28 as defined by its inner surface 112. In some examples, the fluid F is prevented from leaking into the vessel V by a seal between the distal and proximal balloon member segments 106, 110 and the distal and proximal balloon control bands 24, 36 and/or the distal bonding portion 26 and the shaft mounting portion 38. Movement of the fluid F into the axial chamber 174 may be permitted by the handle 12 and the proximal shaft portion 14.

When the balloon 28 is expanded/inflated, the outer surface 114 of the balloon 28 imparts a radially, outwardly directed force to the inner radial surface $S_{RI}$ of the stent S, such that the outer diameter D7 of the stent S is increased to a diameter that is greater than the diameter D7 at insertion of the apparatus 10 and the stent S is said to be moved to a deployed orientation. Deployment of the stent S may ultimately result in the outer radial surface $S_{RO}$ of the stent S imparting a radially outwardly directed force to the stenosis $V_S$ of the vessel V.

Upon placing the stent S adjacent to and against the stenosis $V_S$ of the vessel V, the fluid F may be removed from the axial chamber 174 of the balloon 28 such that the outer surface 114 of the balloon 28 is retracted radially away from the stent S and stenosis $V_S$ of the vessel V. When the balloon 28 is moved from the expanded/inflated orientation back to the retracted/non-inflated orientation, the inner radial surface $S_{RI}$ of the stent S may remain in place adjacent to and against the stenosis $V_S$ of the vessel V and be no longer in contact with any portion of the delivery apparatus 10. The distal balloon control band 24 and the proximal balloon control band 36 may include an elastic and/or rigid materials that assist in the forcing of the fluid F out of the balloon 28, such that the balloon 28 may be collapsed/retracted to its non-inflated orientation.

Referring now to FIGS. 2 and 6, the second axial/proximal end 84 of the distal shaft mounting portion 38 may be disposed adjacent to and connected/joined to a first axial/distal end 176 of the proximal shaft mounting portion 40. As shown in FIG. 6, the core wire 18 may extend toward the proximal end 10a of the delivery apparatus 10, through the passage 90 of the distal shaft mounting portion 38 and into a passage 178 that may be defined a first inner radial surface 180 of the proximal shaft mounting portion 40. The passage 178 may define an inner diameter that is approximately equal to the diameter D6.

Referring to FIG. 2 and the expanded view in FIG. 4, the core wire 18 may extend further toward the proximal end 10a of the delivery apparatus 10 and through the passage 178 such that the second, axial proximal end segment 46 of the core wire 18 may be disposed within or proximate to a passage 182 of the distal end 14b of the proximal shaft portion 14. The length of passage 182 containing the core wire 18, i.e., the passage 202, may be any suitable distance, allowing for improved attachment and reduced kinking (where proximal shaft portion 14 comprises a catheter) of the proximal shaft portion 14 near the site of attachment to the distal shaft portion 16. In some embodiments, the passage 182 may be defined by an inner surface 184 of the proximal shaft portion 14.

One or more of the second axial end segment 46 of the core wire 18 and an axial/proximal end surface 186 of the proximal shaft mounting portion 40 permits the distal shaft portion 16 to be connected to the proximal shaft portion 14. In some examples, one or more of the axial/proximal end surface 186 of the proximal shaft mounting portion 40 may be disposed adjacent and connected/joined to a first axial/distal end surface 188 of the proximal shaft portion 14.

A second inner radial surface 190 of the proximal shaft mounting portion 40 may define an inner diameter, D8. In some examples, an outer radial surface 192 of the proximal shaft portion 14 may include a diameter that is approximately the same as but less than the diameter D8. The second inner radial surface 190 of the proximal shaft mounting portion 40 may be disposed adjacent to and connected/joined to the outer radial surface 192 of the proximal shaft portion 14.

Referring to FIG. 4, a portion of the core wire 18 near the proximal end 52 can be connected to the inner surface 184 of the proximal shaft portion 14, by any suitable method, such as, for example, laser welding.

Figure 8:
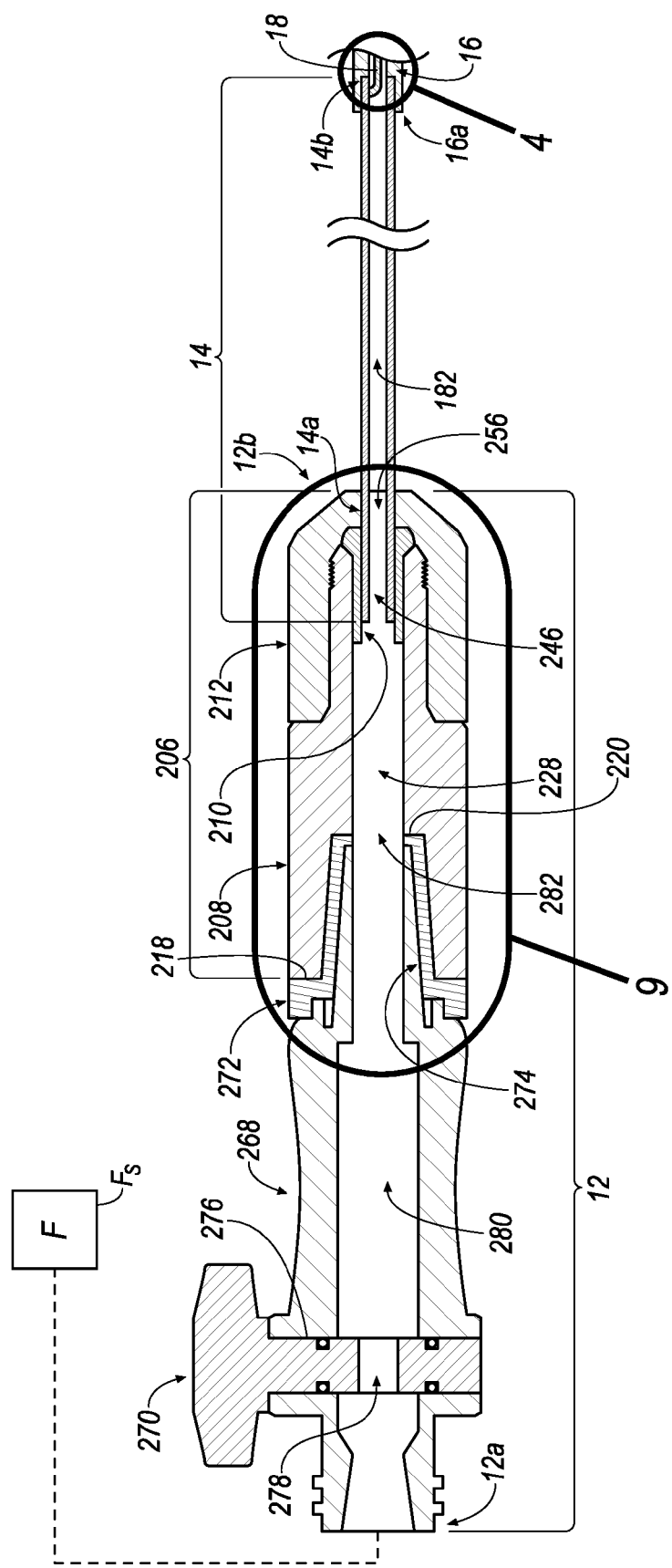
FIG. 8 is a longitudinal-sectional view of an exemplary handle portion of the balloon catheter delivery apparatus, wherein the handle portion includes an optional stop cock.

FIG. 8 depicts an exemplary arrangement of the handle 12, the proximal shaft portion 14 and the proximal end 16a of the distal shaft portion 16. In some implementations, the proximal shaft portion 14 is ultra-violet (UV) adhesive-bonded to the handle 12.

Figure 9:
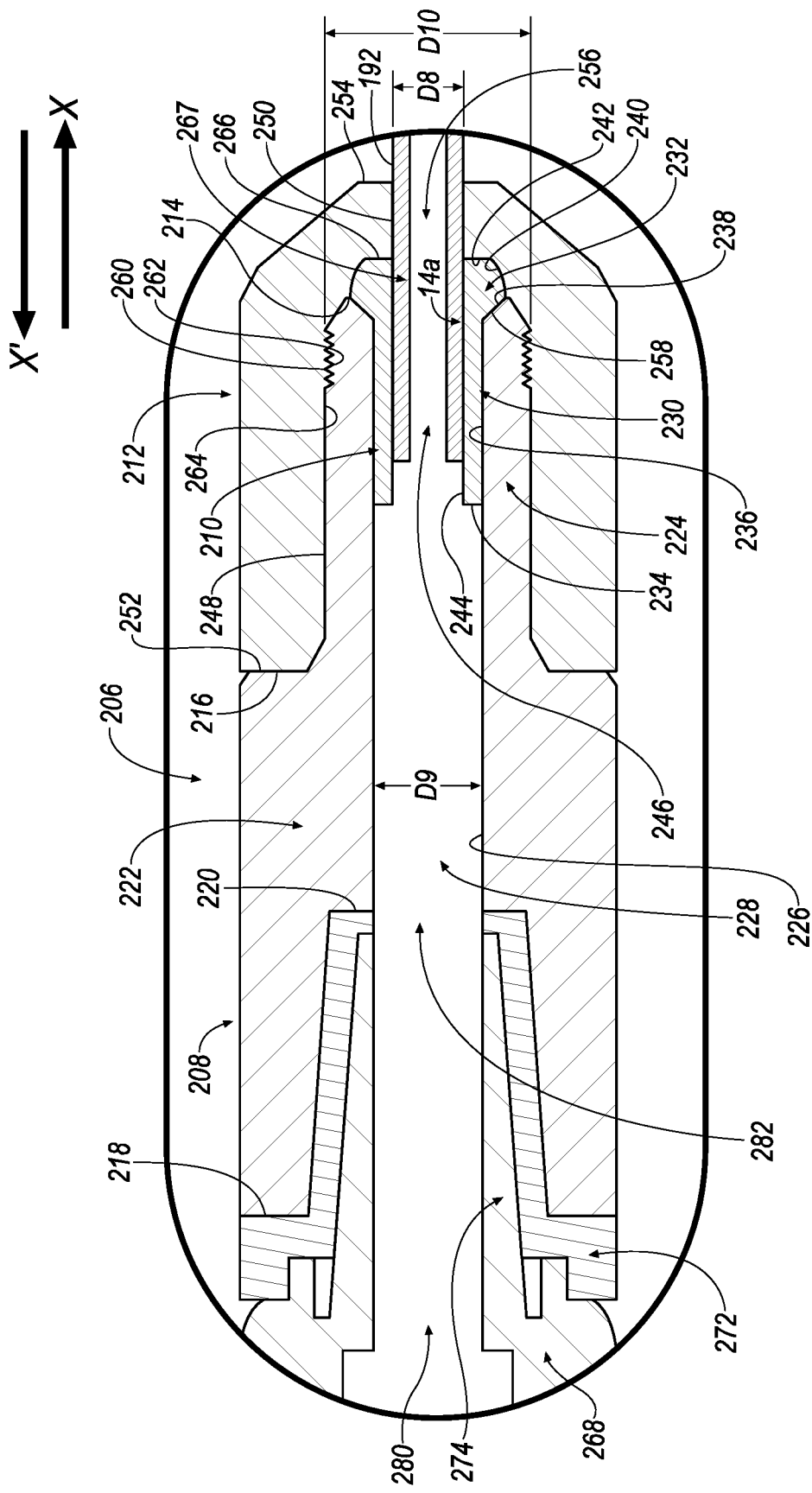
FIG. 9 is an enlarged view of a portion of the handle portion indicated by line 10 of FIG. 8.
Figure 10:
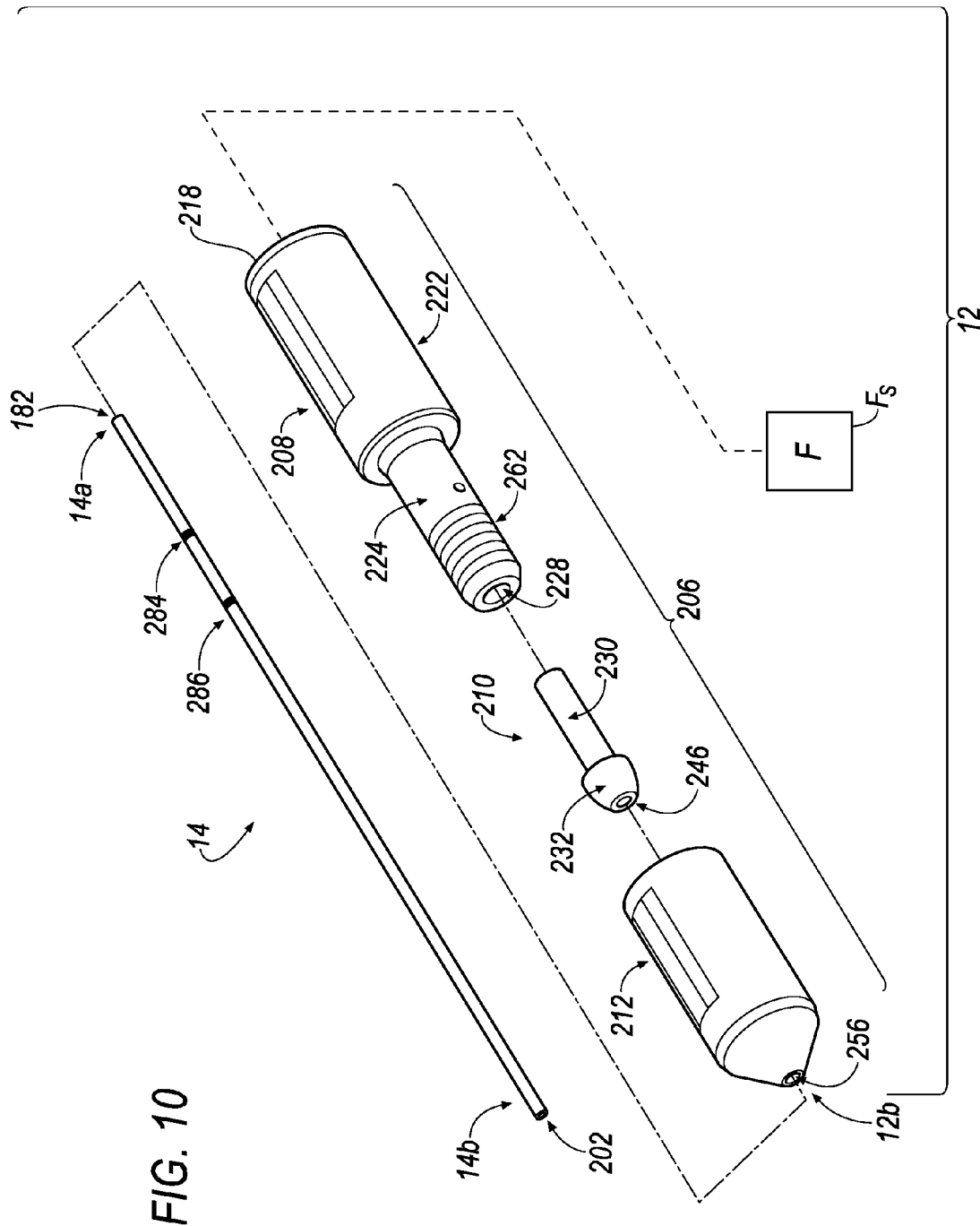
FIG. 10 is a perspective view of an exemplary handle portion and a proximal shaft portion of the balloon catheter apparatus of FIG. 1.

As seen in FIGS. 8-10, the handle 12 may include a docking torque apparatus 206, which may include a base portion 208, a collet portion 210, and a head portion 212. The base portion 208 and the head portion 212 may include an acrylonitrile butadiene styrene (ABS) material. The collet portion 210 may include a brass material. In some examples, where the handle comprises two pieces, the collet portion 210 and the cylindrical socket portion 224 are integral, i.e., combined to form a unitary piece.

Referring to FIG. 9, the base portion 208 may include a first axial/distal end 214, a second axial/distal end 216, a first axial/proximal end 218 and a second axial/proximal end 220. The base portion 208 may include a substantially cylindrical sleeve portion 222 and a substantially cylindrical socket portion 224. The substantially cylindrical sleeve portion 222 may be integrally formed with the substantially cylindrical socket portion 224.

The substantially cylindrical sleeve portion 222 may extend axially from the first axial/proximal end 218 to the second axial/distal end 216. The substantially cylindrical socket portion 224 may extend axially from the second axial/distal end 216 to the first axial/distal end 214.

The base portion 208 may include an inner radial surface 226 that may define an axial passage 228 with an internal diameter D9. The collet portion 210 may include a substantially tubular sleeve portion 230 connected to a chuck portion 232. The substantially tubular sleeve portion 230 may define the collet portion 210 to include a first proximal end surface 234 connected to a first outer radial surface 236 that is connected to a second proximal end surface 238 of the chuck portion 232. The second proximal end surface 238 of the chuck portion 232 may be connected to a second outer radial surface 240 of the chuck portion 232 that is connected to a distal end surface 242 of the chuck portion 232. The substantially tubular sleeve portion 230 and the chuck portion 232 may define an inner radial surface 244 that defines an axial passage 246 that extends axially from the first proximal end surface 234 to the distal end surface 242.

The first outer radial surface 236 of the collet portion 210 may include a diameter approximately equal to but less than the diameter D9 of the axial passage 228 of the base portion 208. The axial passage 246 of the collet portion 210 may include an inner diameter that may be approximately equal to but slightly greater than the outer diameter D8 of the proximal shaft portion 14.

The head portion 212 may include a U-shaped cross-section having a first inner radial surface 248, a second inner radial surface 250, an axial/proximal surface 252 and an axial/distal surface 254. The first inner radial surface 248 may include a diameter D10 that may be approximately similar to, but slightly greater than, an outer diameter of the substantially cylindrical socket portion 224 of the base portion 208. The second inner radial surface 250 may define the head portion 212 to include a passage 256 that is approximately the same as, but slightly greater than, the outer diameter D8 of the proximal shaft portion 14.

The substantially tubular sleeve portion 230 of the collet portion 210 may be axially disposed within the axial passage 228 of the substantially cylindrical socket portion 224 such that the second proximal end surface 238 of the chuck portion 232 may be arranged substantially adjacent/proximate/opposingly facing a chamfered/conical surface 258 of the first axial/distal end 214 of the substantially cylindrical socket portion 224.

The first inner radial surface 248 of the head portion 212 may include a threaded surface 260 that connectably interfaces with a correspondingly-threaded surface 262 formed on an outer radial surface 264 of the substantially cylindrical socket portion 224. The threaded connected of the head portion 212 and the substantially cylindrical socket portion 224 of the base portion 208 permits the head portion 212 to be axially movable according to the direction of arrows, X (i.e., axially toward the distal end 10b), X' (axially toward the proximal end 10a), relative one or more of the base portion 208, collet portion 210 and the proximal end 14a of the proximal shaft portion 14.

As seen in FIG. 9, the proximal shaft portion 14 may be axially inserted through the passage 256 of the head portion 212 and into the axial passage 246 of the collet portion 210. As such, upon axially moving the head portion 212 according to the direction of the arrow, X', an axial/proximal surface 266 of the head portion 212 may come into contact with the distal end surface 242 of the chuck portion 232 such that the second proximal end surface 238 of the chuck portion 232 may come into contact with the chamfered/conical surface 258 of the first axial/distal end 214 of the substantially cylindrical socket portion 224.

As the second proximal end surface 238 comes into contact with the chamfered/conical surface 258, the axial passage 246 of the collet portion 210 at least proximate to the chuck portion 232 may be radially reduced such that the inner radial surface 244, at least proximate to the chuck portion 232, may engage, grip, /or "bite into" a portion 267 of the outer radial surface 192 proximate to at least the proximal end 14a of the proximal shaft portion 14. The engagement of the chuck portion 232 and the proximal end 14a of the proximal shaft portion 14 may provide a frictional, axially-selective connection of the handle 12 and the proximal shaft portion 14.

Referring to FIGS. 8-10, the handle 12 may also include a handle body 268, an optional stopcock 270, and a strain relief member 272. The handle body 268 may axially extend from the proximal end 10a toward the distal end 10b of the delivery apparatus 10 to define a nose portion 274 that is press-fitted to the strain relief member 272. The strain relief member 272 may be axially connected to one or more of the first axial/proximal end 218 and the second axial/proximal end 220 of the base portion 208.

The optional stopcock 270 may be inserted through a radial passage 276 formed in the handle body 268. In some examples, the optional stopcock 270 may be press-fitted to the handle body 268 such that the stopcock 270 may be rotatably connected to the handle body 268 (e.g., to permit the stopcock 270 to be able to turn 90° in a "quarter-turn"

orientation relative to the handle body 268 and within the radial passage 276). The optionally integrated stopcock may effectuate a time savings because the user will not have to assemble the stopcock as an additional part with the delivery apparatus 10.

The stopcock 270 may include an axially-alignable passage 278. Rotation of the stopcock 270 permits the stopcock to act as a valve member to permit or deny movement of the fluid, F, through the handle body 268.

The stopcock 270 may be rotatably-connected to the handle body 268 such that the axial passage 278 of the stopcock 270 may be axially aligned with an axial passage 280 extending through the handle body 268 and an axial passage 282 extending through the strain relief member 272. Accordingly, as seen in FIG. 8, the axial passage 278 may be axially aligned with the axial passages 280, 282 of the handle body 268 and the strain relief member 272. The fluid F may be provided through the axial passages 228, 246, 256, 278, 280, 282 of the handle 12, through the axial passages 182, 202 of the proximal shaft portion 14 and through the axial passages 90, 178 (see, e.g., FIGS. 4 and 6) of the distal shaft portion 12 and into the axial chamber 174 of the balloon 28. The passages 90, 178, 182, 202, 228, 246, 256, 278, 280 and 282 may be in fluid communication with one another and axial chamber 174 in order to permit the fluid F to be moved into the balloon 28 in order to permit the balloon 28 to be moved to an inflated orientation and deploy the stent S.

In some implementations, the handle body 268 does not include the stopcock 270. A valve may be located upstream of the handle body 268 to control flow into the axial passage 280 of the handle body 268.

Referring to FIGS. 1 and 10, the proximal shaft portion 14 may include a stainless steel material and the outer radial surface 192 of the proximal shaft portion may be coated with a polytetrafluoroethylene (PTFE) material. The outer radial surface 192 may include a proximal depth marker 284 and a distal depth marker 286 formed on outer radial surface 192 of the proximal shaft portion 14. The proximal depth marker 284 may be arranged on the outer radial surface 192 approximately 100 centimeters from the distal end 10b of the delivery apparatus 10. The distal depth marker 286 may be arranged on the outer radial surface 192 approximately 90 centimeters from the distal end 10b of the delivery apparatus 10.

Referring to FIGS. 2, 5 and 7, the proximal marker band 32 and the distal marker band 34 may be formed on the radial outer surface 42 of the core wire 18. The proximal marker band 32 permits a user to gauge the approximate axial location of where the proximal segment 110 and intermediate segment 108 of the balloon 28 are joined together. The distal marker band 34 permits the user to know of an approximate axial location of where the distal segment 106 and intermediate segment 108 of the balloon 28 are joined together. As such, by knowing the location of the segments 106-110 of the balloon 28, the user may also know the approximate axial location of the stent S as well.

Each of the proximal and distal marker bands 32, 34 may include an inner radial surface 288 and an outer radial surface 290. The inner radial surface 288 may be connectively swaged to the radial outer surface 42 of the core wire 18. The proximal and distal marker bands 32, 34 may include any desirable material, such as, for example, a platinum-iridium material.

Referring to FIGS. 1 and 2, one or more protective tubular members 292 may be arranged coaxially relative to the core wire 18 and the proximal and distal marker bands 32, 34.

The protective tubular member 292 may include an inner radial surface 294 and an outer radial surface 296. The outer radial surface 296 may define an outer diameter D11. The inner radial surface 294 may be arranged adjacent to the outer radial surface 290 of the proximal and distal marker bands 30, 32. The protective tubular member 292 may include any desirable material, such as a polymer. An example of a polymer material includes, without limitation, a polyamide material.

The protective tubular member 292 may prevent the inner surface 112 of the balloon 28 from contacting the outer radial surface 290 of the proximal and distal marker bands 32, 34. By preventing the inner surface 112 of the balloon 28 from contacting the outer radial surface 290 of the proximal and distal marker bands 32, 34, any axial shifting of the proximal and distal marker bands 32, 34 relative the core wire 18 may be reduced/eliminated as the delivery apparatus 10 is being inserted into the vessel, V. In addition, the protective tubular member 292 may prevent the stent from being compressed to a diameter so small that it cannot be properly deployed.

In some implementations, the distal shaft portion 16 of the delivery apparatus 10 may be coated with a friction-reducing material that may assist a user in the inserting or removing the delivery apparatus 10. The coating may include a hydrophillic coating, which may include a polymer-based material. Not every element 18-40 of the distal shaft portion 16 may be coated with the friction-reducing material. For example, the balloon 28 may not be coated with the friction-reducing material. Further, although the stent S may not necessarily be considered to be part of the delivery apparatus 10, the stent S may also not be coated with the friction-reducing material.

A protective polytetrafluoroethylene (PTFE) tubular sheath (not shown) may be arranged about the outer radial surface $S_{RO}$ of the stent S or the catheter tubing. The sheath may be provided with the delivery apparatus 10 if, for example, the stent S is arranged relative to the delivery apparatus in a "pre-mounted" configuration. Accordingly, prior to utilizing the delivery apparatus 10, a user may remove the sheath in order to expose the stent S.

In some implementations, the axial core wire 18 may include a stainless steel material. Moreover, the distal balloon control band 24 may include a polyurethane material and the handle body 268 may include a polycarbonate (PC) material. The stopcock 270 may include an acetal material. The strain relief member 272 may include a thermoplastic polyether material, a polybutylene material, a terphthalate material, a polyether glycol material or the like.

One or more of the structures of the shaft portions 18-40, may include a material that lends itself to having a non-rigid, shapeable quality. Further, one or more of the structures 18-40 may include a material that lends itself to having similar or dissimilar durometers (i.e., softness/hardness ratings). Further, although the distal shaft portion 16 is described to include structures identified at 18-40, the distal shaft portion 16 is not limited to the number of, type or geometry of structure identified at 18-40 and that the invention may be practiced with any desirable number of, type or geometry of structure.

The balloon 28 may be folded upon itself one or more times. Accordingly, although the balloon 28 is illustrated in FIGS. 1, 2, 5, 6, and 7 to include one, non-folded layer, the illustration of the balloon 28 in the figures does not limit the disclosed structure or function of the invention. Various balloon folding, combinable with this disclosure, can be found in U.S. Pat. No. 6,071,285 and U.S. Pat. No. 6,120,533, which are hereby incorporated by reference in their entireties.

Referring to FIGS. 11 and 12, the distal shaft portion 16 is shown prior to inflation. FIGS. 11 and 12 also illustrate a "folded balloon" in which the balloon is folded upon itself. Although, for simplicity, the balloon is shown as being folded on itself three times, the balloon can be folded in any manner. FIG. 11 (and also FIG. 2) clearly shows the placement of the balloon control bands 24 and 36 over the inflatable balloon 28 during manufacturing. Specifically, the proximal balloon control band 36 extends in the proximal direction beyond the proximal end of the balloon 28 and the distal balloon control band extends in the distal direction beyond the distal end of the balloon 28. In addition, in FIG. 11, a gap is clearly seen between the distal end of the proximal balloon control band 36 and the proximal end of the stent S as well as between the proximal end of the distal balloon control band 24 and the distal end of the stent S. This gap allows the stent S to be mounted on the balloon 28 as the final step after the balloon angioplasty catheter has been assembled. This differs from the embodiments taught by Fischell et al. in U.S. Pat. Nos. 6,375,660, 6,936,065 and 7,011,673 where the balloon control bands touch the stent without a gap. This would require that the balloon control bands be placed after the stent is mounted which is a much more difficult manufacturing process.

In some implementations, the balloon delivery apparatus includes a catheter comprising a proximal hypotube portion, a distal flexible tube portion, and a lumen disposed longitudinally through the proximal hypotube portion and distal flexible tube portion. The balloon delivery apparatus also includes a balloon having a proximal end that is affixed to a distal shaft mounting portion of the proximal hypotube portion and a distal end that is affixed to a core wire at a location proximal to the distal tip of the core wire. The balloon can be coaxial with the core wire and in fluid communication with the lumen of the proximal hypotube portion and the distal flexible tube portion. The balloon delivery apparatus includes a plurality of balloon control bands, wherein at least one balloon control band is located at the proximal end of the balloon and at least one balloon control band is located at the distal end of the balloon. The balloon control bands may restrict the balloon's longitudinal expansion upon inflation.

In some examples, the proximal hypotube portion comprises a first material and the distal flexible tube section comprises a second material. For example, the proximal hypotube portion comprises a metal. In additional examples, the proximal hypotube portion comprises stainless steel. And in some instances, the stainless steel is coated with PTFE. The proximal hypotube section may further include a plurality of optical markers (e.g., depth markers). The distal flexible tube portion may comprise a polymer material, which may comprise a silicone rubber material.

In some implementations, the distal tip of the core wire further comprises a prolate spherical or hemispherical cap. The core wire further comprises a coiled section wherein the coiled section is located proximal to the distal tip. The core wire may include a plurality of depth markers, wherein at least one depth marker is located approximately concentrically with the proximal end of the balloon and at least one depth marker is located approximately concentrically with the distal end of the balloon. Optionally, the core wire includes at least one protective tubular member having a length approximately equal to the length of the balloon, wherein the protective tubular member is coaxial with the core wire and the balloon. For example, the protective tubular member can be disposed between the depth marker located approximately concentrically with the proximal end of the balloon and the depth marker can be located approximately concentrically with the distal end of the balloon. In some examples, the balloon control bands comprise an elastomer material that elastically expands upon inflation of the balloon.

In some implementations, the balloon is a non-compliant balloon comprising a polymer material. For instance, the balloon comprises a polyamide polymer material.

In some examples, the apparatus includes a handle affixed to the proximal hypotube portion. The handle may include an inflation control that controls the inflation of the balloon.

In some implementations, the balloon delivery catheter apparatus includes a catheter comprising a proximal hypotube, a distal flexible tube, and a lumen that extends longitudinally throughout both tubes. The balloon delivery catheter apparatus also includes a balloon near the distal end of the proximal hypotube that fluidly communicates with the lumen. The balloon includes a distal end, a proximal end, and an intermediate segment. A core wire extending throughout at least a portion of the catheter lumen and beyond the distal end of the balloon includes a proximal end, a distal tip, and a coiled member. The coiled member can be disposed between the proximal end and the distal tip. A proximal balloon control band may be concentrically arranged around the proximal end of the balloon, and a distal balloon control band may be concentrically arranged about the distal end of the balloon. The distal and proximal balloon control bands may restrict inflation of the balloon at the proximal and distal ends of the balloon. The distal and proximal balloon control bands may comprise an elastomer material that elastically expands during inflation of the balloon and contracts upon deflation.

In some examples, a bonding element coaxially mounted about the coiled member of the core wire secures the distal end of the balloon to the coil member.

A portion of the distal balloon control band may be affixed to the distal end of the balloon. The proximal end of the balloon can be affixed to the distal end the proximal hypotube, and the proximal balloon control band can be affixed to the proximal hypotube. Or, the proximal balloon control band can be affixed to the proximal end of the balloon. In additional examples, the proximal end of the core wire is affixed to the distal end of the proximal hypotube.

In some examples, a plurality of depth markers are affixed to the catheter (e.g., affixed to the proximal hypotube). Moreover, at least one depth marker may be approximately concentric with the proximal end of the balloon and at least one depth marker may be approximately concentric with the distal end of the balloon.

A protective tubing member, having a proximal end and a distal end, may be affixed to the core wire so that the proximal end of the member is approximately concentric with the proximal end of the balloon, and the distal end of the member is approximately concentric with the distal end of the balloon.

In some implementations, the distal tip comprises a round surface comprising a hemisphere or prolate hemisphere. The balloon may comprise a polyamide polymer material (e.g., a polyamide material (e.g., Nylon)).

The proximal hypotube may comprise a first material and the distal flexible tube may comprise a second material. For example, the proximal hypotube may comprise stainless steel. In some instances, the stainless steel is substantially coated with a polymer material comprising PTFE. Moreover, the distal flexible tube may comprise a polymer material comprising silicone rubber.

Upon inflation, the balloon may adopt a geometry having two inward facing cones and a cylindrical segment located between said cones.

In some implementations, a handle may be connected to and in fluid communication with the lumen of the proximal hypotube. The handle may include a docking torque apparatus having a base portion, a collet portion disposed within a passage of the base portion (208), and a head portion movably connected to the base portion. The head portion may be selectively engagable with the collet portion. The proximal shaft section of the hypotube may be disposable through one or more of the head portion, the collet portion, or the base portion. In some examples, the handle includes a strain relief member connected to the handle body and/or the base portion.

A method of treating vascular stenosis in a patient may include providing a balloon delivery apparatus that includes a handle having a handle body, a catheter having a hypotube section, a distal shaft section, and a lumen extending longitudinally throughout both sections. The hypotube section may be connected to the handle body, and the handle body may be in fluid communication with the lumen. The balloon delivery apparatus includes a balloon having a distal segment, an intermediate segment, and a proximal segment, each of which is defined by an inner surface and an outer surface. The proximal segment of the balloon may be affixed to the distal end of the hypotube section and in fluid communication with the lumen of the hypotube section. The balloon delivery apparatus includes a distal balloon control band having an inner surface, an outer surface, and a proximal end surface and a proximal balloon control band having an inner surface, an outer surface and a distal end surface. The inner surface of the distal balloon control band is adjacent to the outer surface of the distal segment of the balloon. The inner surface of the proximal balloon control band is adjacent to the outer surface of the proximal segment of the balloon member. A core wire extends through a portion of the distal shaft section and entirely through the balloon. The handle slidably engages the hypotube section of the catheter, and rotational movement of the handle longitudinally advances or retracts the core wire, the hypotubes section, the distal shaft section, or any combination thereof. Several methods further comprise inserting the balloon into a blood vessel of a patient. And some methods comprise advancing the balloon sufficiently into the vessel such that a portion of the intermediate segment of the balloon is approximately concentric with the stenosis. Some methods further comprise inflating the balloon such that the stenosis is at least partially alleviated. And, some methods further comprise deflating the balloon member and removing the balloon from the patient.

Figure 15:
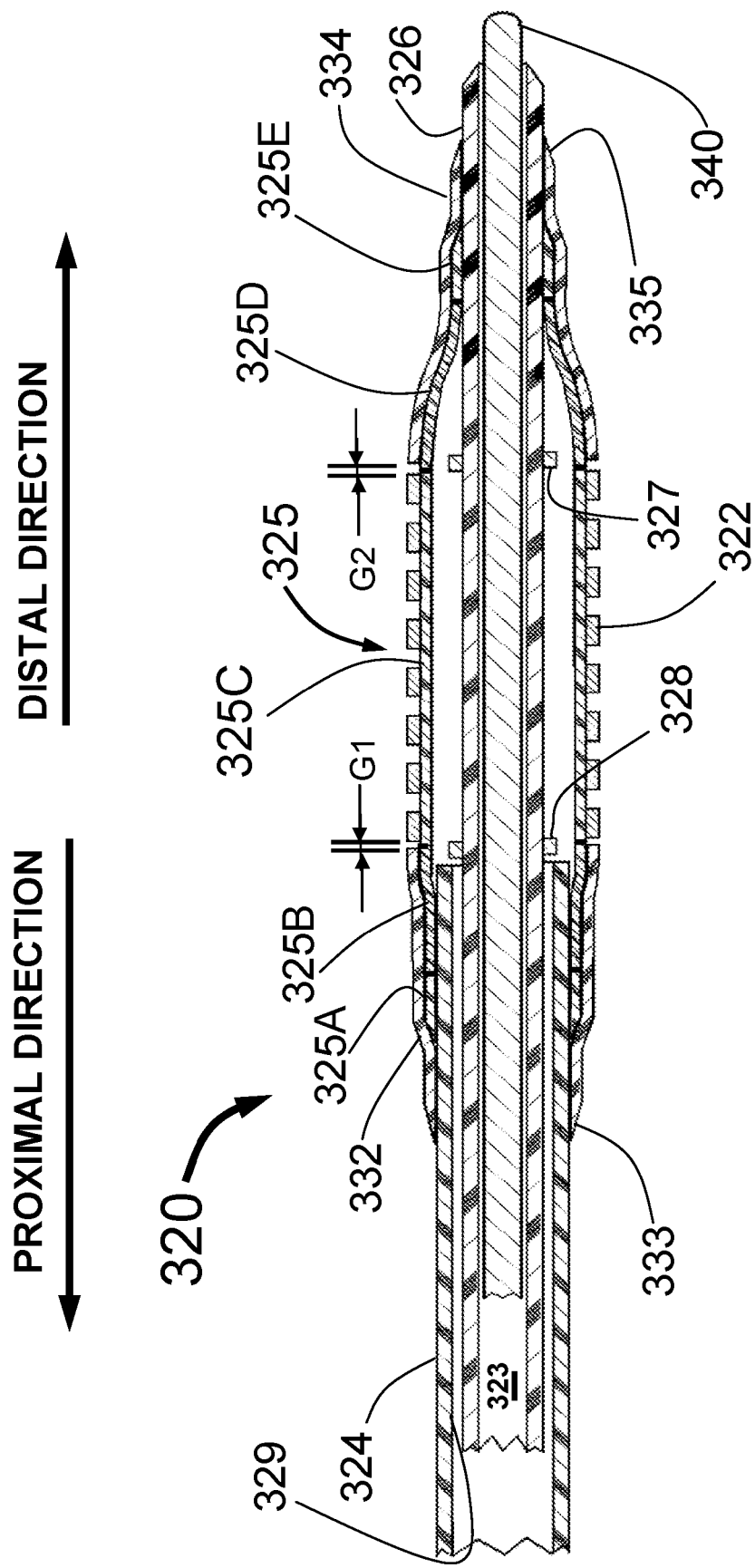
FIG. 15 is a longitudinal cross section of an exemplary distal end of a balloon angioplasty catheter for stent delivery of either a rapid exchange or over-the wire type.

FIG. 15 provides a cross-section of a distal portion of a stent delivery catheter 320. It would be typical of either an over-the-wire stent delivery catheter or a rapid exchange stent delivery catheter to have its distal portion to be formed as is shown in FIG. 15.

The stent delivery catheter 320 illustrated in FIG. 15 has an inner tube 326 with an interior lumen 323 through which a guide wire 340 can be placed. It would be typical of such a stent delivery catheter 320 to be advanced over a guide wire 340 that would have been previously placed into a blood vessel of the patient. The stent delivery catheter 320 also has an outer tube 324 which forms a doughnut shaped lumen 329 between the inner surface of the outer tube 324 and the exterior surface of the inner tube 326. This doughnut (torroidal) shaped lumen 329 provides a passageway through which pressurized normal saline solution can be used to inflate a balloon 325. The lumen 329 may also be used to deflate the balloon 325 after a stent 322 has been placed into a stenosis. The stent delivery catheter 320 may include proximal and distal radiopaque marker bands 327, 328 that indicate under fluoroscopy the proximal and distal ends of the stent 322.

In some implementations, the balloon 325 includes five sections which are described (from its proximal end to its distal end) as follows:

1) A proximal cylindrical shaft 325A which is a cylindrical section fixedly joined to the outer tube 324.

2) A proximal conical section 325B attached at its proximal end to the proximal cylindrical shaft 325A and attached at its distal end to the central cylindrical section 325C of the balloon 325.

3) A central cylindrical section 325C attached at its proximal end to the proximal conical section 325B and attached at its distal end to the distal conical section 325D.

4) A distal conical section 325D attached at its proximal end to the central cylindrical section 325C and attached at its distal end to the distal cylindrical shaft 325E.

5) A distal cylindrical shaft 325E attached at its proximal end to the distal conical section 325D and fixedly joined to a distal portion of the inner tube 326.

Although the proximal conical section 325B is not clearly shown in FIG. 15 to be of a conical shape, it can take that conical shape when the balloon 325 is inflated. Angioplasty balloons such as the balloon 325 are typically made from a polymeric material such as nylon, formed in their final desired shape and then folded or wrapped to the pre-deployment diameter shown in FIG. 15. It should be noted that the balloon 325 may be represented by as a single layer structure. The balloon 325 can have several folds prior to inner tubular shaft inflation.

Also shown in FIG. 15 are a proximal balloon control band 332 and a distal balloon control band 334. Although the proximal balloon control band 332 might extend in the proximal direction over only the proximal cylindrical shaft 325A of the balloon 325, it may extend over the outer tube 324, creating a smooth transition from the outer tube 324 to the stent 322. Although the distal balloon control band 332 might extend in the distal direction over only the distal cylindrical shaft 325A of the balloon 325, it may extend over the inner tube 324, creating a smooth transition from the inner tube 324 to the stent 322. Smooth transitions in a stent delivery catheter improve the deliverability of the stent in tortuous vessels of the human body such as the coronary arteries. The balloon control bands 332, 334 may be made from a highly elastic polymer such as polyurethane or silicone rubber.

The balloon control bands 332, 334 may be used in conjunction with the stent 322 to prevent stent embolization or movement of the stent 322 off the balloon in the proximal direction which can result in poor deployment. Specifically, the balloon control bands 332, 334, as shown in FIG. 15, can prevent embolization of any stent 322. Another important feature of the balloon control band 332 is that, in some examples, it extends proximal to the balloon proximal shaft 325A and has a tapered proximal end 333 that improves the stent delivery catheter's ability to be easily pulled back into the guiding catheter through which it is placed. The distal balloon control band 334 may extend distally beyond the balloon distal shaft 325E and have a tapered distal end 335 for improving the ability of the stent delivery catheter 320 to be pushed through a tight stenosis or though a tortuous arterial anatomy. The outside diameter of the distal balloon control band 334 may be equal to or greater than the diameter of the stent 322, creating a contour of the outer surface of the stent delivery catheter 320 which improves the ability of the stent delivery catheter 320 to penetrate through a tight stenosis or navigate around a sharp bend.

The balloon control bands 332, 334 may assist with (1) refolding the balloon after it is inflated, (2) preventing bulging at the ends of the balloon during stent expansion (which is called "dog-boning,") which can cause arterial restenosis, (3) providing a smooth tapered leading edge stent delivery system 320 so that the stent more easily can be pushed through a tight stenosis or around tight bends, (4) the distal balloon control band can have an outside diameter that is greater than the outside diameter of the stent 322 so that there is not a step up in diameter for the stent 322 as is the case for conventional balloon expandable stent delivery systems, thus making it is easier to push the stent 322 through a tight stenosis; and (5) the interior edges of both retention bands can keep the stent 322 positioned onto only the central cylindrical section 325C of the balloon 325 so that the stent 322 stays over the central cylindrical section 325C of the balloon and is properly deployed when the balloon 325 is inflated. Thus, the balloon control bands 332 and 334 provide a multiplicity of advantages for the stent delivery catheter 320. These same advantages of course apply to the stent-on-a-wire embodiments shown in FIGS. 2, 11 and 16.

As can be seen in FIG. 15, there should be a small distance G1 that separates the distal end of the proximal balloon control band 332 from the proximal end of the stent 322 and a distance G2 that separates the proximal end of the distal balloon control band from the distal end of the stent 322. This differs from the prior art by Fischell, et al, where the stent ends touch the edges of the balloon control bands. Each of the distances G1 and G2 should be greater than 0.1 mm and less than 2.0 mm. The purpose of these distances G1 and G2 is to allow for uncertainly in manufacturing for the actual length of the stents compared with the actual separation distance between the inner edges of the balloon control bands 332 and 334. In addition, the distances G1 and G2 reduce the need for longitudinal positional accuracy as the stent 322 is crimped down onto the balloon 325 in manufacturing the product. Similar gaps between the balloon control bands and mounted stent are shown for the stent-on-a-wire embodiment of FIGS. 11 and 16.

In the preferred embodiment of the present invention, the proximal balloon control band 332 is fixedly attached to the stent delivery system 320 proximal to the balloon proximal conical section 325B. For example, the proximal balloon control band 332 would be fixedly attached to both the outer tube 324 and the balloon proximal cylindrical shaft 325A but not attached to the balloon's proximal conical section 325B. During balloon inflation, this allows the balloon 325, including the proximal conical section 325B, to unfold and slide underneath the portion of the proximal balloon control band 332 that lies over the proximal conical section 325B of the balloon 325.

Similarly, the distal balloon control band 334 is fixedly attached to the stent delivery system 320 distal to the balloon distal conical section 325D. For example, the distal balloon control band 334 would be fixedly attached to both the inner tube 326 and the balloon distal cylindrical shaft 325E but not attached to the balloon distal conical section 325D. During balloon inflation, this allows the balloon 325 including the distal conical section 325D to unfold and slide underneath the portion of the distal balloon control band 334 that lies over the distal conical section 325D of the balloon 325.

These attachment methods for the balloon control bands 322 and 334 are also applicable to the balloon control bands 24 and 25 of FIG. 11.

Although the term "balloon control bands" has been used throughout this description, an equally good name for these structures is "stent retention bands" as a major purpose of these elements is to prevent stent embolization.

Figure 16:
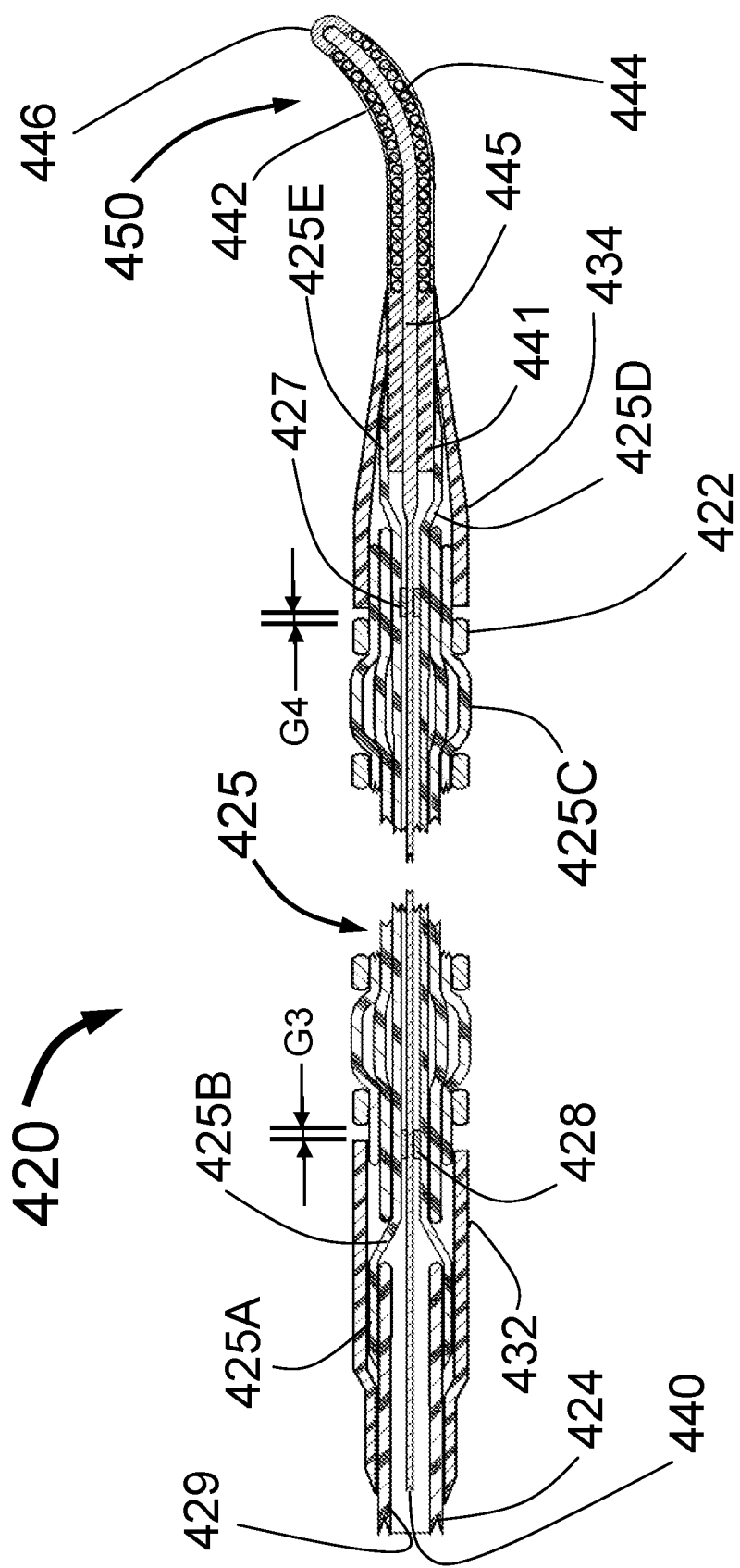
FIG. 16 is a longitudinal cross section of an exemplary distal end of a balloon angioplasty catheter having a fixed guide wire.

FIG. 16 is a cross-section of the distal portion of a stent-on-a-wire embodiment of the present invention which is a fixed wire stent delivery catheter 420 which illustrates several novel features of the present invention.

The stent delivery catheter 420 illustrated in FIG. 16 has a core wire 440 that extends into the distal tip 450 of the catheter 420. The stent delivery catheter 420 also has an outer tube 424 which forms a doughnut shaped lumen 429 between the inner surface of the outer tube 424 and the exterior surface of the core wire 440. This doughnut (torroidal) shaped lumen provides the passageway through which pressurized normal saline solution is typically used to inflate the balloon 425. The lumen 429 is also used to deflate the balloon 425 after the stent 422 has been placed into a stenosis. The stent delivery catheter 420 also has radiopaque marker bands 427 and 428 that indicate under fluoroscopy the proximal and distal ends of the stent 422.

The balloon 425 has five sections which are described (from its proximal end to its distal end) as follows:

1) The proximal cylindrical shaft 425A which is a cylindrical section that is fixedly joined to the outer tube 424.

2) The proximal conical section 425B that is attached at its proximal end to the proximal cylindrical shaft 425A and attached at its distal end to the central cylindrical section 425C of the balloon 425.

3) The central cylindrical section 425C that is attached at its proximal end to the proximal conical section 425B and attached at its distal end to the distal conical section 425D.

4) The distal conical section 425D that is attached at its proximal end to the central cylindrical section 425C and attached at its distal end to the distal cylindrical shaft 425E.

5) The distal cylindrical shaft 425E that is attached at its proximal end to the distal conical section 425D and is fixedly joined to the outside of the distal tip 450.

Also shown in FIG. 16 are the proximal balloon control band 432 and the distal balloon control band 434. Although the proximal balloon control band 432 might extend in the proximal direction over only the proximal cylindrical shaft 425A of the balloon 425, in the preferred embodiment of the present invention, it extends over the outer tube 424 creating a smooth transition from the outer tube 424 to the stent 422. Although the distal balloon control band 432 might extend in the distal direction over only the distal cylindrical shaft 425A of the balloon 425, in the preferred embodiment of the present invention, it extends over the inner tube 424 creating a smooth transition from the inner tube 424 to the stent 422. Smooth transitions in a stent delivery catheter will improve the deliverability of the stent in tortuous vessels of the human body such as the coronary arteries. The balloon control bands 432, 434 can be made from a highly elastic polymer such as polyurethane or silicone rubber.

The balloon control bands 432, 434 may be used in conjunction with the stent 422 to prevent stent embolization or movement of the stent 422 off the balloon 425 in the proximal direction which can result in poor deployment. For example, the balloon control bands 432, 434, examples of which are shown in FIG. 16, may prevent embolization of any stent 422. The proximal balloon control band 432 may extend proximal to the balloon proximal shaft 425A and have a tapered proximal end that improves stent delivery catheter's ability to be easily pulled back into the guiding catheter through which it is placed. The distal balloon control band 434 may extend distally beyond the balloon distal shaft 425E and have a tapered distal end that improves the ability of the stent delivery catheter 420 to be pushed through a tight stenosis. The outside diameter of the distal balloon control band 434 may be equal to or greater than the outside diameter of the stent 422, creating a contour for the outer surface of the stent delivery catheter 420 that improves the ability of the stent delivery catheter 420 to penetrate through a tight stenosis or navigate around a sharp bend.

The balloon control bands 432, 434 may aid (1) refolding the balloon after it is inflated, (2) preventing bulging at the ends of the balloon during stent expansion (which is called "dog-boning"), which can cause arterial restenosis, (3) providing a smooth tapered leading edge stent delivery system 420 so that the stent 422 can be more easily pushed through a tight stenosis or around tight bends, (4) making it is easier to push the stent 422 through a tight stenosis, as by having an outside diameter of the distal balloon control band that is greater than the outside diameter of the stent 422 so that there is not a step up in diameter for the stent 422 as is the case for conventional balloon expandable stent delivery systems; and (5) keeping the stent 422 positioned onto only the central cylindrical section 425C of the balloon 425 using the interior edges of both balloon control bands 432, 434 so that the stent 422 stays over that central cylindrical section 425C of the balloon and is properly deployed when the balloon 425 is inflated.

As can be seen in FIG. 16, a small distance G3 may separate the distal end of the proximal balloon control band 432 from the proximal end of the stent 422 and a distance G4 may separate the proximal end of the distal balloon control band from the distal end of the stent 422. This differs from the prior art by the Fischell patents (noted earlier), where the stent ends touch the edges of the balloon control bands. In some implementations, each of the distances G3, G4 are greater than 0.1 mm and less than 2.0 mm. These distances G3, G4 may allow for uncertainly in manufacturing for the actual length of the stents compared with the actual separation distance between the inner edges of the balloon control bands 432, 434. In addition, the distances G3, G4 may reduce the need for longitudinal positional accuracy as the stent 422 is crimped down onto the balloon 425 in manufacturing the product. Similar gaps between the balloon control bands 432, 434 and mounted stent are shown for the stent-on-a-wire implementation shown in FIG. 11 and the implementation shown in FIG. 15 that is adapted to be advanced over a guide wire.

In some implementations, the distal tip 450 of the catheter 420 has a central wire 445 that connects to the core wire 440. The proximal end of the distal tip 450 may have a plastic sleeve 441 covering the central wire 445 so that the distal cylindrical shaft 425E of the balloon 425 can be more easily attached to the distal tip 450. The central portion of the distal tip 450 may have a helical wire 444 wrapped around the central wire 445. The distal portion of the distal tip 450 may have an end piece 446 attached to the distal end of the central wire 445. A lubricity coating 442 may cover the outer surface of the distal tip 450. It is also envisioned that a lubricity coating may cover the entire outer surface of the catheter 420 except for the balloon 425 and stent 422.

In some implementations, the proximal balloon control band 432 is fixedly attached to the stent delivery system 420 proximal to the balloon proximal conical section 425B. For example, the proximal balloon control band 432 can be fixedly attached to both the outer tube 424 and the balloon proximal cylindrical shaft 425A, but not attached to the balloon's proximal conical section 425B. During balloon inflation, this allows the balloon 425, including the proximal conical section 425B, to unfold and slide underneath the portion of the proximal balloon control band 432 that lies over the proximal conical section 425B of the balloon 425. The distal balloon control band 434 can be fixedly attached to the stent delivery system 420 distal to the balloon distal conical section 425D. For example, the distal balloon control band 434 can be fixedly attached to both the plastic sleeve 441 and the balloon distal cylindrical shaft 425E, but not attached to the balloon distal conical section 425D. During balloon inflation, this allows the balloon 425 including the distal conical section 425D to unfold and slide underneath the portion of the distal balloon control band 434 that lies over the distal conical section 425D of the balloon 325.

In some implementations, a stent delivery catheter 320, 420 includes a catheter tubing 324, 424 defining a lumen therethrough, a balloon 325, 425 disposed near a distal end of the catheter tubing 324, 424 and moving between deflated and inflated states, and proximal and distal balloon control bands 332, 334, 432, 434 concentrically arranged around a respective proximal end portion (e.g., a proximal cylindrical shaft 325A, 425A and/or a proximal conical section 325B, 425B) and a respective distal end portion (e.g., a distal conical section 325D, 425D and/or a distal cylindrical shaft 325E, 425E) of the balloon 325. The proximal balloon control band 332, 334 has a proximal end located proximally of a proximal end of the balloon 325 and a distal end located adjacent a proximal end of a received unexpanded stent 322, 422. The distal balloon control band 334, 434 has a proximal end located adjacent a distal end of the received unexpanded stent 322, 422 and a distal end located distally of a distal end of the balloon 325, 425. The balloon control bands 332, 334, 432, 434 may each have a diametric cross-section larger than the balloon 325, 425 in an uninflated state and the unexpanded stent 322, 422 received over the balloon 325, 425 to impede axial movement of the unexpanded stent 322, 422 off of the balloon 325, 425.

In some implementations, each balloon control band 332, 334, 432, 434 comprises an elastic material that expands during inflation of the balloon 325, 425 and contracts upon deflation of the balloon 325, 425. The proximal and distal balloon control bands 332, 334 may be secured to the respective proximal and distal end portions of the balloon 325, 425. Moreover, the proximal end portion of the balloon 325, 425 and the proximal balloon control band 332, 432 can both be attached to the catheter tubing 324, 424. In some examples, the proximal balloon control band 332, 432 is attached at least partially to the balloon 325, 425 and at least partially to the catheter tubing 324, 424. In additional examples, the distal balloon control band 334, 434 is attached at least partially to the balloon 325, 425 and at least partially to a core wire 445. Each balloon control band 332, 334, 432, 434 may have a non-uniform cross-sectional thickness ΔD along an axial direction of the balloon control band. In some implementations, each balloon control band 332, 334, 432, 434 has first and second end portions. The first end portion may have a larger diametric cross-section $DC_A$ than the second end portion. Moreover, the first end portion of each balloon control band 332, 334, 432, 434 may be disposed adjacent to a received stent on the balloon.

In some implementations, a method of manufacturing a medical device includes disposing a balloon 325, 425 near a distal end of a catheter tubing 324, 424. The balloon 325, 425 is movable between deflated and inflated states. The method further includes disposing an unexpanded stent 322, 422 over the balloon 325, 425 in an uninflated state, arranging a proximal balloon control band 332, 432 concentrically around a proximal end portion of the balloon 325, 425 (e.g., a proximal cylindrical shaft 325A, 425A and/or a proximal conical section 325B, 425B), and arranging a distal balloon control band 334, 434 concentrically around a distal end portion of the balloon 325, 425 (e.g., a distal conical section 325D, 425D and/or a distal cylindrical shaft 325E, 425E). The proximal balloon control band 332, 432 has a proximal end located proximally of a proximal end of the balloon 325, 425 and a distal end located adjacent a proximal end of the unexpanded stent 322, 422. The distal balloon control band 334, 434 has a proximal end located adjacent a distal end of the unexpanded stent 322, 422 and a distal end located distally of a distal end of the balloon 325, 425. The balloon control bands 332, 334, 432, 434 may each have a diametric cross-section larger than the balloon 325, 425 in an uninflated state and the unexpanded stent 322, 422 received over the balloon 325, 425 to impede axial movement of the unexpanded stent off of the balloon.

In some implementations, each balloon control band 332, 334, 432, 434 comprises an elastic material that expands during inflation of the balloon 325, 425 and contracts upon deflation of the balloon. The method may include at least partially securing the proximal and distal balloon control bands 332, 334, 432, 434 to the respective proximal and distal end portions of the balloon 325, 425. In some examples, the method includes affixing the proximal end portion of the balloon 325, 425 and the proximal balloon control band 332, 432 both to the catheter tubing 324, 424. In additional examples, the method includes shaping the balloon control bands 332, 334, 432, 434 to have a non-uniform cross-sectional thickness along an axial direction of the balloon control bands. Each balloon control band 332, 334, 432, 434 has first and second end portions. The first end portion may have a larger diametric cross-section than the second end portion. The method may include arranging the first end portion of each balloon control band 332, 334, 432, 434 adjacent to a received stent 322, 422 on the balloon 325, 425.

In some implementations, a method of treating vascular stenosis includes inserting into a vessel of a patient a portion of a stent delivery catheter 320, 420. The stent delivery catheter 320, 420 includes a catheter tubing 324, 424 defining a lumen therethrough, a balloon 325, 425 disposed near a distal end of the catheter tubing 324, 424 and moving between deflated and inflated states, and proximal and distal balloon control bands 332, 334, 432, 434 concentrically arranged around a respective proximal end portion (e.g., a proximal cylindrical shaft 325A, 425A and/or a proximal conical section 325B, 425B) and a respective distal end portion (e.g., a distal conical section 325D, 425D and/or a distal cylindrical shaft 325E, 425E) of the balloon 325. The proximal balloon control band 332, 334 has a proximal end located proximally of a proximal end of the balloon 325 and a distal end located adjacent a proximal end of a received unexpanded stent 322, 422. The distal balloon control band 334, 434 has a proximal end located adjacent a distal end of the received unexpanded stent 322, 422 and a distal end located distally of a distal end of the balloon 325, 425. The balloon control bands 332, 334, 432, 434 may each have a diametric cross-section larger than the balloon 325, 425 in an uninflated state and the unexpanded stent 322, 422 received over the balloon 325, 425 to impede axial movement of the unexpanded stent 322, 422 off of the balloon 325, 425. The method includes advancing the balloon across the vascular stenosis, inflating the balloon to compress the vascular stenosis, deflating the balloon, and removing the stent delivery catheter from the patient.

In some implementations, a balloon angioplasty catheter 320, 420 includes a catheter tubing 324, 424 defining a lumen therethrough, and an inflatable balloon 325, 425 having a central cylindrical portion 325C, 425C, a distal portion having a distal conical portion 325D, 425D and a distal cylindrical shaft 325E, 425E, and a proximal portion having a proximal conical portion 325B, 425B and a proximal cylindrical shaft 325A, 425A. The proximal shaft 325A, 425A of the inflatable balloon 325, 425 can be fixedly attached to a distal end of the catheter tubing 324, 424. A balloon control band 334, 434 is mounted coaxially over the distal portion of the inflatable balloon 325, 425. The balloon control band 334, 434 extends in a distal direction beyond the distal shaft 325E, 425E of the inflatable balloon 325, 425 and has a proximal end located near a proximal end of the distal conical section 325D, 425D of the balloon 325, 425 when the balloon is in an uninflated state. In this configuration, a proximal balloon control band 332, 432 is not necessarily needed or used.

In some implementations, the balloon angioplasty catheter 320, 420 includes a balloon expandable stent 322, 422 having a proximal end and a distal end. The stent 322, 422 is mounted coaxially onto the central cylindrical section 325C, 425C of the inflatable balloon 325, 425 with the distal end of the stent 322, 422 adjacent the proximal end of the balloon control band 334, 434. In some examples, a separation distance G2, G4 between the distal end of the stent 322, 422 and the proximal end of the balloon control band 334, 434 is less than about 2 mm. The balloon angioplasty catheter 320, 420 may include a fixed guide wire 440, 445 extending in a distal direction beyond the distal end of the distal balloon shaft 325E, 425E. In some examples, the balloon control band 334, 434 has a diametric cross-section larger than the balloon 325, 425 in an uninflated state and an unexpanded stent 322, 422 received over the balloon 325, 425 to impede axial movement of the unexpanded stent 322, 422 off of the balloon 325, 425. For example, a maximum outer diameter of the balloon control band 334, 434 may be within 1.0 mil of an outside diameter of an unexpanded stent 322, 422 received by the balloon 325, 425. Moreover, a maximum outer diameter of the balloon control band 334, 434 can be between 1.0 mil and 3.0 mils greater than an outer diameter of an unexpanded stent 322, 422 received by the balloon 325, 425.

A number of implementations have been described. Nevertheless, it will be understood that various modifications may be made without departing from the spirit and scope of the disclosure. Accordingly, other implementations are within the scope of the following claims.

What is claimed is:

1. A balloon delivery catheter apparatus comprising:
   a catheter tubing defining a lumen therethrough and having proximal and distal ends;
   a balloon disposed near a distal end of the catheter tubing and moving between deflated and inflated states;
   a core wire having a proximal end attached to the catheter tubing inside the lumen and extending distally away and substantially co-axially with the catheter tubing through the balloon to a distal free end;
   proximal and distal balloon control bands concentrically arranged around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation, wherein the balloon control bands each have a diametric cross-section larger than the balloon in its uninflated state and an unexpanded stent received over the balloon to impede axial movement of the unexpanded stent off of the balloon;

a coil disposed around the core wire, the coil having a proximal end attached to at least one of the distal end portion of the balloon and the distal balloon control band; and a handle received by the proximal end of the catheter tubing, the handle comprising:
 a handle base defining a handle lumen therethrough;
 a collet received at least partially in the handle lumen at a distal end portion of the handle base, the collet defining a collet lumen therethrough; and
 a handle head releasably connected to the distal end portion of the handle base over the collet, the handle head defining an aperture axially aligned with the collet lumen and sized to receive the proximal end of the catheter tubing therethrough and at least partially in the collet lumen,
 wherein the handle lumen is in fluid communication with the lumen of the received catheter tubing, and
 wherein movement of the handle head toward the handle base causes constriction of the collet about the received catheter tubing.

2. The balloon delivery catheter apparatus of claim 1, wherein the proximal and distal balloon control bands are secured to the respective proximal and distal end portions of the balloon.

3. The balloon delivery catheter apparatus of claim 1, wherein the proximal end portion of the balloon and the proximal balloon control band are both attached to the catheter tubing.

4. The balloon delivery catheter apparatus of claim 3, wherein the proximal balloon control band is attached at least partially to the balloon and at least partially to the catheter tubing.

5. The balloon delivery catheter apparatus of claim 1, wherein the distal balloon control band is attached at least partially to the balloon and at least partially to the core wire.

6. The balloon delivery catheter apparatus of claim 1, wherein each balloon control band has a non-uniform cross-sectional thickness along an axial direction of the balloon control band.

7. The balloon delivery catheter apparatus of claim 6, wherein each balloon control band has first and second end portions, the first end portion having a larger diametric cross-section than the second end portion, the first end portion of each balloon control band disposed adjacent to a received stent on the balloon.

8. The balloon delivery catheter apparatus of claim 1, wherein the balloon and the balloon control bands are coaxially disposed about the core wire.

9. The balloon delivery catheter apparatus of claim 1, wherein the coil extends beyond the distal end portion of the balloon.

10. The balloon delivery catheter apparatus of claim 1, wherein the balloon control bands restrict expansion of at least the end portions of the balloon to a threshold diameter.

11. The balloon delivery catheter apparatus of claim 1, wherein the collet comprises:
 a substantially tubular section having an outer diameter less than or equal to a diameter of the handle lumen; and
 a chuck attached to the substantially tubular section and having an outer diameter larger than the handle lumen, the chuck defining a chamfered surface arranged to engage an opposing chamfered surface of the handle base;
 wherein movement of the handle head toward the handle base causes movement of the collet toward the handle base and the chamfered surface of the handle base to exert a substantially radially inward force on the opposing chamfered surface of the chuck.

12. The balloon delivery catheter apparatus of claim 1, wherein the handle head is threadably received by the distal end portion of the handle base.

13. The balloon delivery catheter apparatus of claim 1, wherein the handle further comprises a valve member disposed on a proximal end portion of the handle base.

14. The balloon delivery catheter apparatus of claim 1, wherein the handle further comprises a strain relief disposed on at least one of the handle base and the handle head.

15. A balloon delivery catheter apparatus comprising:
 a catheter tubing defining a lumen therethrough and having proximal and distal ends;
 a balloon disposed near a distal end of the catheter tubing and moving between deflated and inflated states, the balloon having a proximal end portion and a distal end portion;
 a core wire having a proximal end attached near the distal end of the catheter tubing inside the lumen and extending distally away and substantially co-axially with the catheter tubing through the balloon to a distal free end;
 a coil disposed around the core wire, the coil having a proximal end attached to the distal end portion of the balloon;
 a balloon support tube co-axially disposed over the core wire and within the balloon, wherein the balloon support tube prevents compression of the balloon below a threshold diameter; and
 a handle received by the proximal end of the catheter tubing, the handle comprising:
  a handle base defining a handle lumen therethrough;
  a collet received at least partially in the handle lumen at a distal end portion of the handle base, the collet defining a collet lumen therethrough; and
  a handle head releasably connected to the distal end portion of the handle base over the collet, the handle head defining an aperture axially aligned with the collet lumen and sized to receive the proximal end of the catheter tubing therethrough and at least partially in the collet lumen,
  wherein the handle lumen is in fluid communication with the lumen of the received catheter tubing, and
  wherein movement of the handle head toward the handle base causes constriction of the collet about the received catheter tubing.

16. The balloon delivery catheter apparatus of claim 15, wherein the balloon support tube prevents compression of a received stent over the balloon to a diameter less than a threshold un-deployed stent diameter.

17. The balloon delivery catheter apparatus of claim 15, wherein the balloon support tube has an axial length less than or equal to an axial length of the balloon.

18. The balloon delivery catheter apparatus of claim 15, wherein the balloon support tube is attached to the core wire so that a proximal end of the balloon support tube is approximately concentric with a proximal end of the balloon, and a distal end of the balloon support tube is approximately concentric with a distal end of the balloon.

19. The balloon delivery catheter apparatus of claim 15, wherein the balloon support tube comprises a polyamide material.

\* \* \* \* \*

UNITED STATES PATENT AND TRADEMARK OFFICE
CERTIFICATE OF CORRECTION

PATENT NO. : 9,585,781 B2
APPLICATION NO. : 15/085281
DATED : March 7, 2017
INVENTOR(S) : Fischell et al.

Page 1 of 1

It is certified that error appears in the above-identified patent and that said Letters Patent is hereby corrected as shown below:

On the Title Page

In Column 1, under "Related U.S. Application Data", Line 1, delete "(60)" and insert --(63)-- therefor In the Specification In Column 10, Line 53, delete "58" and insert --20-- therefor In Column 19, Line 22, delete "12" and insert --16-- therefor In Column 24, Line 43, delete "332" and insert --334-- therefor In Column 24, Line 46, delete "324," and insert --326,-- therefor In Column 24, Line 47, delete "324" and insert --326-- therefor In Column 26, Line 50, delete "432" and insert --434-- therefor In Column 28, Line 56, delete "445." and insert --440.-- therefor Signed and Sealed this
Nineteenth Day of August, 2025

Coke Morgan Stewart
*Acting Director of the United States Patent and Trademark Office*